United States Patent [19]
Whitfield et al.

[11] Patent Number: 5,833,696
[45] Date of Patent: Nov. 10, 1998

[54] APPARATUS FOR APPLYING SURGICAL CLIPS

[75] Inventors: Kenneth H. Whitfield, New Haven; Martin J. Nohilly, Trumbull; George M. Chelednik, Bethel, all of Conn.

[73] Assignee: United States Surgical Corporation, Norwalk, Conn.

[21] Appl. No.: 725,181

[22] Filed: Oct. 3, 1996

[51] Int. Cl.⁶ .................................................. A61B 17/12
[52] U.S. Cl. ............................................................ 606/143
[58] Field of Search ................................... 606/139, 143, 606/142, 144, 148

[56] References Cited

U.S. PATENT DOCUMENTS

| D. 276,650 | 12/1984 | Green et al. . |
|---|---|---|
| 2,008,367 | 7/1935 | Rhinevault . |
| 2,741,248 | 11/1956 | Woodhall . |
| 2,968,041 | 1/1961 | Skold . |
| 3,585,985 | 6/1971 | Gould . |
| 3,603,310 | 9/1971 | Mottia et al. . |

(List continued on next page.)

FOREIGN PATENT DOCUMENTS

| 0068046 | 1/1983 | European Pat. Off. . |
|---|---|---|
| 0112980 | 7/1984 | European Pat. Off. . |
| 0406724 | 1/1991 | European Pat. Off. . |
| 0409569 | 1/1991 | European Pat. Off. . |
| 500353A-1 | 8/1992 | European Pat. Off. . |
| 656190 | 6/1995 | European Pat. Off. . |
| 704190 | 4/1996 | European Pat. Off. . |
| 769274 | 4/1997 | European Pat. Off. . |
| 2679763 | 2/1993 | France . |
| 2330182 | 2/1975 | Germany . |
| 2546696 | 4/1976 | Germany . |
| 3802651 | 8/1989 | Germany . |
| 19504000 | 8/1996 | Germany . |
| 1093329 | 5/1984 | U.S.S.R. . |
| 2054384 | 2/1981 | United Kingdom . |
| 8202825 | 9/1982 | WIPO . |
| 8900514 | 10/1989 | WIPO . |
| 8910094 | 11/1989 | WIPO . |

OTHER PUBLICATIONS

Information Booklet for "Auto Suture® Premium Surgiclip™ Titanium Disposable Automatic Clip Appliers", ©1988, 1989.
"Ligaclip For Security in Ligation", Ethicon 1982.
"Deep Surgery Advantage: Dramatic New Access Plus Automatic–Feed in Vessel Ligation", Weck, Surgery, Gynecology & Obstertrics, Sep. 1986.

(List continued on next page.)

Primary Examiner—Michael Powell Buiz
Assistant Examiner—Vikki Trinh

[57] ABSTRACT

A surgical clip applying instrument is disclosed which includes a handle portion, a body extending distally from the handle portion and defining a longitudinal axis, and a plurality of surgical clips disposed within the body. A jaw assembly is mounted adjacent a distal end portion of the body. The jaw assembly includes first and second jaw portions movable between a spaced-apart and an approximated position. A clip pusher is provided to individually distally advance a distalmost surgical clip to the jaw assembly while the jaw portions are in the spaced-apart position. An actuator at least partially disposed within the body is longitudinally movable in response to actuation of the handle portion. A jaw closure member is positioned adjacent the first and second jaw portions to move the jaw portions to the approximated position. The actuator and the jaw closure member define an interlock therebetween to produce simultaneous movement of the actuator and the jaw closure member when the actuator is positioned adjacent the distal end portion of the body.

19 Claims, 34 Drawing Sheets

U.S. PATENT DOCUMENTS

| | | |
|---|---|---|
| 3,631,707 | 1/1972 | Miller . |
| 3,777,538 | 12/1973 | Weatherly et al. . |
| 3,780,416 | 12/1973 | Rider . |
| 3,834,392 | 9/1974 | Lampman et al. . |
| 3,848,773 | 11/1974 | Adler et al. . |
| 3,856,016 | 12/1974 | Davis . |
| 3,870,048 | 3/1975 | Yoon . |
| 3,882,854 | 5/1975 | Hulka et al. . |
| 3,954,108 | 5/1976 | Davis . |
| 3,955,581 | 5/1976 | Spasiano et al. . |
| 3,967,625 | 7/1976 | Yoon . |
| 3,989,049 | 11/1976 | Yoon . |
| 4,027,510 | 6/1977 | Hilterbrandt . |
| 4,038,987 | 8/1977 | Komiya . |
| 4,064,881 | 12/1977 | Meredith . |
| 4,084,594 | 4/1978 | Moslor . |
| 4,088,743 | 5/1978 | Yoon . |
| 4,101,063 | 7/1978 | Kapitanov et al. . |
| 4,103,680 | 8/1978 | Yoon . |
| 4,152,920 | 5/1979 | Green . |
| 4,166,466 | 9/1979 | Jarvik . |
| 4,169,476 | 10/1979 | Hiltebrandt . |
| 4,185,762 | 1/1980 | Froehlich . |
| 4,188,953 | 2/1980 | Klieman et al. . |
| 4,196,836 | 4/1980 | Becht . |
| 4,226,239 | 10/1980 | Polk et al. . |
| 4,226,242 | 10/1980 | Jarvik . |
| 4,228,895 | 10/1980 | Larkin . |
| 4,230,116 | 10/1980 | Watson . |
| 4,240,411 | 12/1980 | Hosono . |
| 4,241,734 | 12/1980 | Kandel et al. . |
| 4,242,902 | 1/1981 | Green . |
| 4,246,903 | 1/1981 | Larkin . |
| 4,257,419 | 3/1981 | Göltner et al. . |
| 4,273,129 | 6/1981 | Boebel . |
| 4,296,751 | 10/1981 | Blake, III et al. . |
| 4,299,224 | 11/1981 | Noiles . |
| 4,316,468 | 2/1982 | Klieman et al. . |
| 4,325,376 | 4/1982 | Klieman et al. . |
| 4,325,377 | 4/1982 | Boebel . |
| 4,335,928 | 6/1982 | Barrett et al. . |
| 4,338,947 | 7/1982 | Williams . |
| 4,367,746 | 1/1983 | Derechinsky . |
| 4,372,316 | 2/1983 | Blake, III et al. . |
| 4,374,523 | 2/1983 | Yoon . |
| 4,393,883 | 7/1983 | Smyth et al. . |
| 4,394,864 | 7/1983 | Sandhaus . |
| 4,412,539 | 11/1983 | Jarvik . |
| 4,425,915 | 1/1984 | Ivanov . |
| 4,430,997 | 2/1984 | DiGiovanni et al. . |
| 4,440,170 | 4/1984 | Golden et al. . |
| 4,450,839 | 5/1984 | Transue . |
| 4,452,357 | 6/1984 | Klieman et al. . |
| 4,452,376 | 6/1984 | Klieman et al. . |
| 4,471,780 | 9/1984 | Menges et al. . |
| 4,471,781 | 9/1984 | Di Giovanni et al. . |
| 4,479,489 | 10/1984 | Tucci . |
| 4,480,641 | 11/1984 | Faila et al. . |
| 4,481,952 | 11/1984 | Pawelec . |
| 4,492,232 | 1/1985 | Green . |
| 4,505,414 | 3/1985 | Filipi . |
| 4,509,518 | 4/1985 | McGarry et al. . |
| 4,512,345 | 4/1985 | Green . |
| 4,522,207 | 6/1985 | Klieman et al. . |
| 4,532,925 | 8/1985 | Blake, III . |
| 4,534,351 | 8/1985 | Rothfuss et al. . |
| 4,549,544 | 10/1985 | Favaron . |
| 4,550,715 | 11/1985 | Santangelo et al. . |
| 4,556,058 | 12/1985 | Green . |
| 4,557,263 | 12/1985 | Green . |
| 4,558,706 | 12/1985 | Nakada et al. . |
| 4,562,839 | 1/1986 | Blake, III et al. . |
| 4,572,183 | 2/1986 | Juska . |
| 4,576,166 | 3/1986 | Montgomery et al. . |
| 4,589,421 | 5/1986 | Ullman . |
| 4,598,711 | 7/1986 | Deniega . |
| 4,611,595 | 9/1986 | Klieman et al. . |
| 4,616,650 | 10/1986 | Green et al. . |
| 4,624,254 | 11/1986 | McGarry et al. . |
| 4,633,882 | 1/1987 | Matsuo et al. . |
| 4,646,740 | 3/1987 | Peters et al. . |
| 4,649,904 | 3/1987 | Krauter et al. . |
| 4,662,373 | 5/1987 | Montgomery et al. . |
| 4,662,374 | 5/1987 | Blake, III . |
| 4,674,504 | 6/1987 | Klieman et al. . |
| 4,682,491 | 7/1987 | Pickard . |
| 4,686,965 | 8/1987 | Bonnet et al. . |
| 4,691,853 | 9/1987 | Storace . |
| 4,700,694 | 10/1987 | Shishido . |
| 4,712,549 | 12/1987 | Peters et al. . |
| 4,759,364 | 7/1988 | Boebel . |
| 4,784,137 | 11/1988 | Kulik et al. . |
| 4,841,888 | 6/1989 | Mills et al. . |
| 4,850,350 | 7/1989 | Jackson . |
| 4,850,355 | 7/1989 | Brooks et al. . |
| 4,858,608 | 8/1989 | McQuilkin . |
| 4,874,364 | 10/1989 | Morris et al. . |
| 4,900,307 | 2/1990 | Kulli . |
| 4,919,152 | 4/1990 | Ger . |
| 4,935,010 | 6/1990 | Cox et al. . |
| 4,944,443 | 7/1990 | Oddsen et al. . |
| 4,967,949 | 11/1990 | Sandhaus . |
| 5,030,226 | 7/1991 | Green et al. . |
| 5,040,715 | 8/1991 | Green et al. . |
| 5,047,038 | 9/1991 | Peters et al. . |
| 5,049,152 | 9/1991 | Simon et al. . |
| 5,067,958 | 11/1991 | Sandhaus . |
| 5,071,430 | 12/1991 | de Salis et al. . |
| 5,084,057 | 1/1992 | Green et al. . |
| 5,100,418 | 3/1992 | Yoon et al. . |
| 5,100,420 | 3/1992 | Green et al. . |
| 5,104,394 | 4/1992 | Knoepfler . |
| 5,104,395 | 4/1992 | Thornton et al. . |
| 5,112,343 | 5/1992 | Thornton . |
| 5,163,945 | 11/1992 | Ortiz et al. . |
| 5,171,247 | 12/1992 | Hughett et al. . |
| 5,171,249 | 12/1992 | Stefanchik et al. . |
| 5,176,702 | 1/1993 | Bales et al. . |
| 5,192,288 | 3/1993 | Thompson et al. . |
| 5,199,566 | 4/1993 | Ortiz et al. . |
| 5,207,691 | 5/1993 | Nardella . |
| 5,246,156 | 9/1993 | Rothfuss et al. . |
| 5,246,450 | 9/1993 | Thronton et al. . |
| 5,258,007 | 11/1993 | Spetzler et al. . |
| 5,282,807 | 2/1994 | Knoepfler . |
| 5,282,808 | 2/1994 | Kovac et al. . |
| 5,290,299 | 3/1994 | Fain et al. . |
| 5,306,280 | 4/1994 | Bregen et al. . |
| 5,333,772 | 8/1994 | Rothfuss et al. . |

OTHER PUBLICATIONS

"New Surgical Procedures For Indirect Hernias", Innovative Surgical Devices, Inc., 1989.

"Laparoscopic Sterilization with Spring Clips", Richard Wolf Instruction Manual, pp. 1–28.

"Information About Dimethyl Silicone Compounds", Dow Corning Corporation.

"Laparoscopic Sterilization With Electrocautery, Spring–Loaded Clips, And Silastic Bands: Technical Problems And Early Complications", Fertility And Sterility, vol. 27, No. 3, pp. 256–266.

"A Clip Applicator For Laparoscopic Sterilization", Fertility And Sterility, vol. 27, No. 9, pp. 1036–1039.

"Laparoscopic Sterilization With Spring–Loaded Clips: Double–Puncture Technique", The Journal Of Reproductive Medicine, May, 1977, vol. 18, No. 5, pp. 241–245.

"Laparoscopic Sterilization With The Spring Clip: Instrumentation Development And Current Clinical Experience", American Journal Of Obstetrics And Gynecology, Dec. 15, 1979, vol. 135, No. 8, pp. 1016–1020.

"An Applicator For The Hulka Fallopian Tube Clip", American Journal Of Obstetrics And Gynecology, Mar. 15, 1981, vol. 139, No. 6, pp. 665–668.

"Metal Clip Techniques Utilizing Pistol Grip Appliers", The American Journal Of Surgery, Feb. 1982, pp. 274–276.

"Results Of Experimental Endoscopic Esophageal Varix Ligation", The American Surgeon, Jan. 1988, vol. 54, pp. 105–108.

"The Hemoclip® X20", Surgery Gynecology & Obstetrics, Sep. 1986, vol. 163, No. 3.

"Laparoscopy": Acknowledgements, Preface, Contributors, Contents, Contemporary Instruments, Silicone Ring, Chapter 32—Television in Laparoscopy, Chapter 34—Nongynecologic Laparoscopy, Copyright 1977, The Williams & Wilkins Company, 46 pgs.

"Falope Ring Band System", Cabot Medical, 13 pgs.

"Instructions for Use of Autostat", Axiow Medical, 2 pgs.

"It's Your Choice for Tubal Sterilization", The Journal of Reproductive Medicine, vol. 26, No. 1, Jan. 1981, 1 pg.

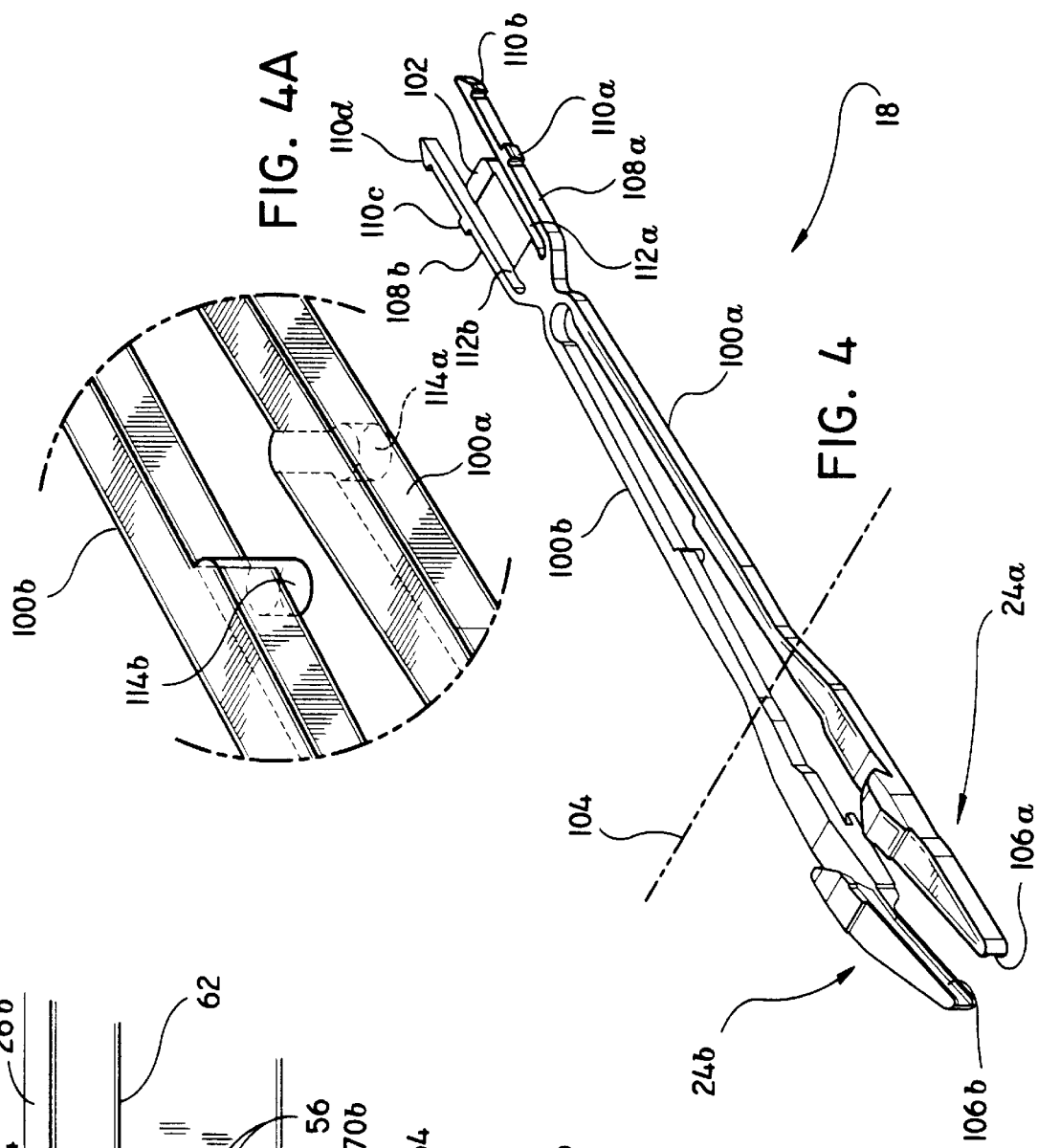
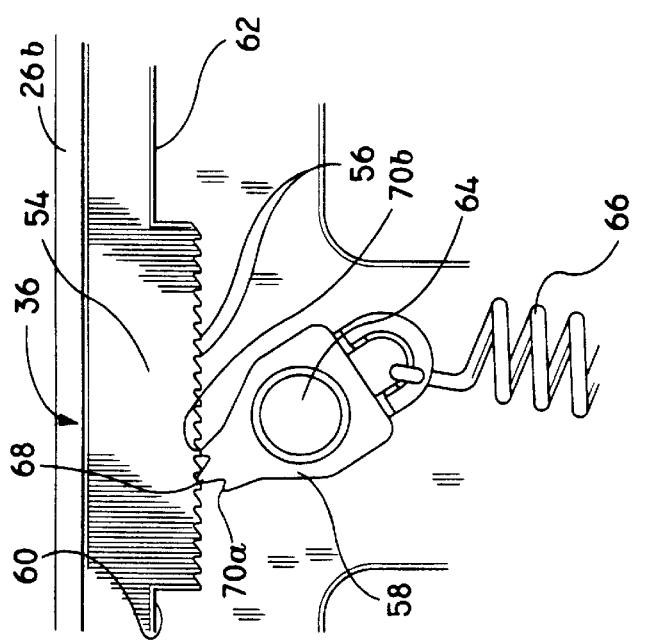

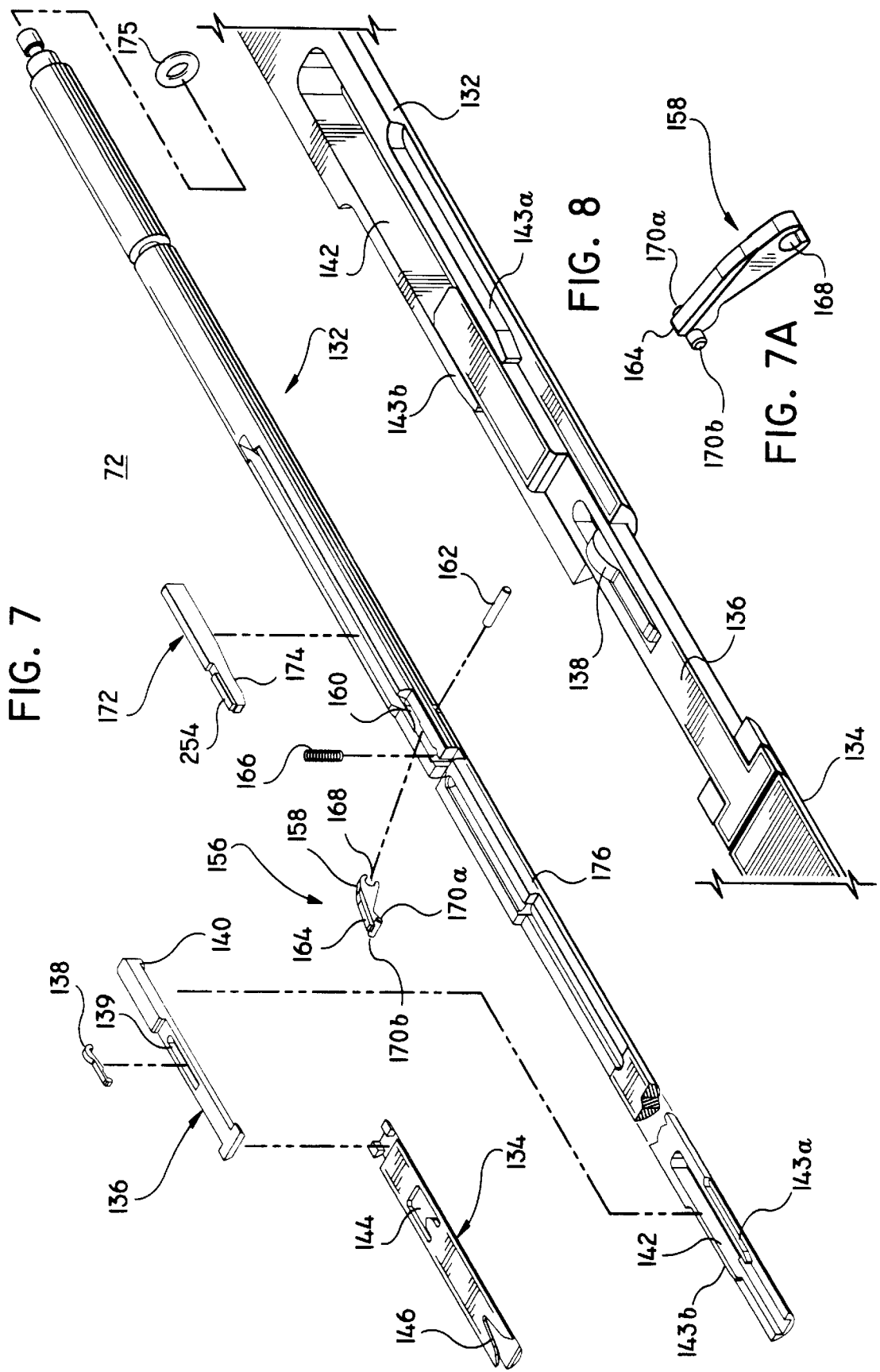

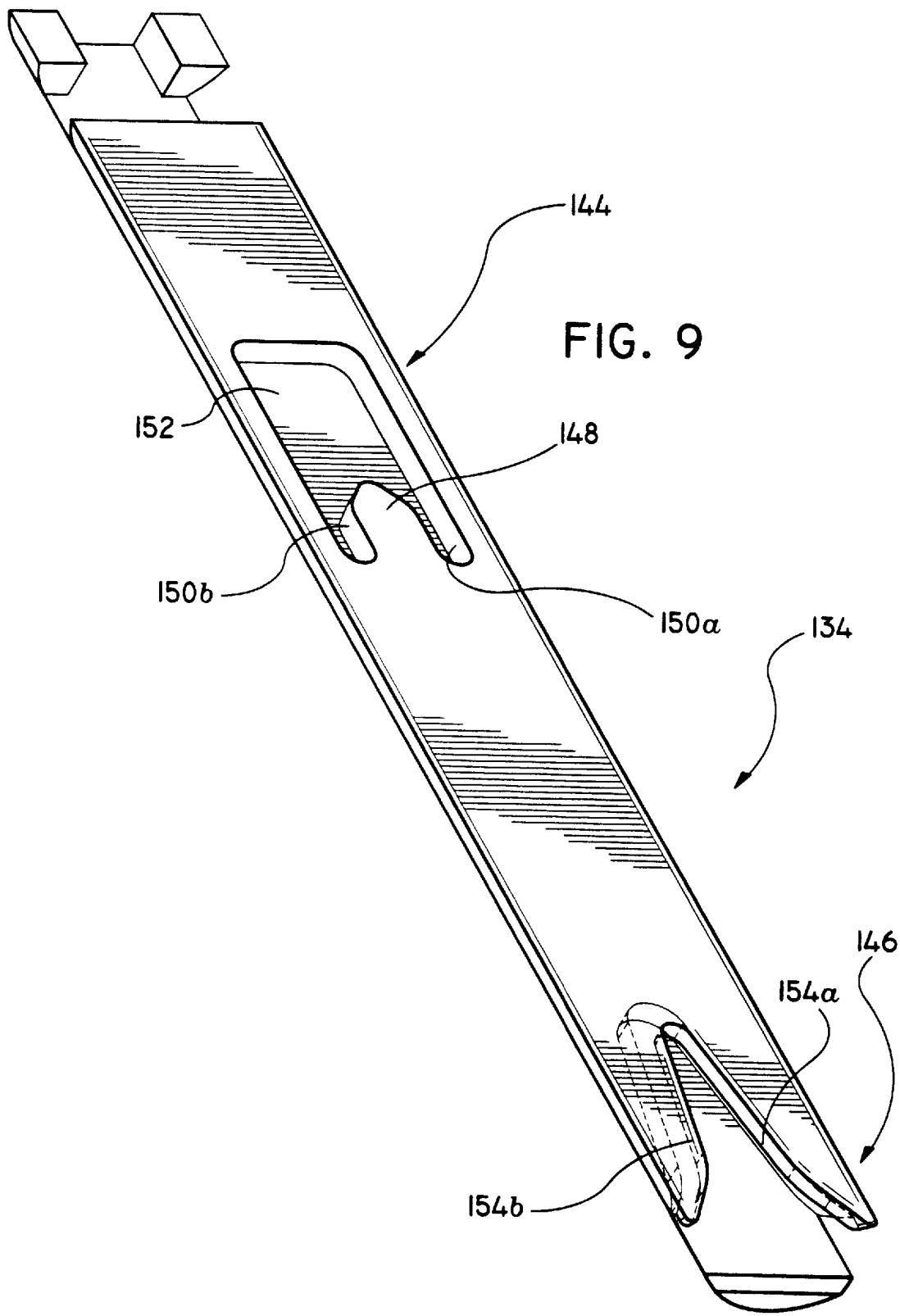

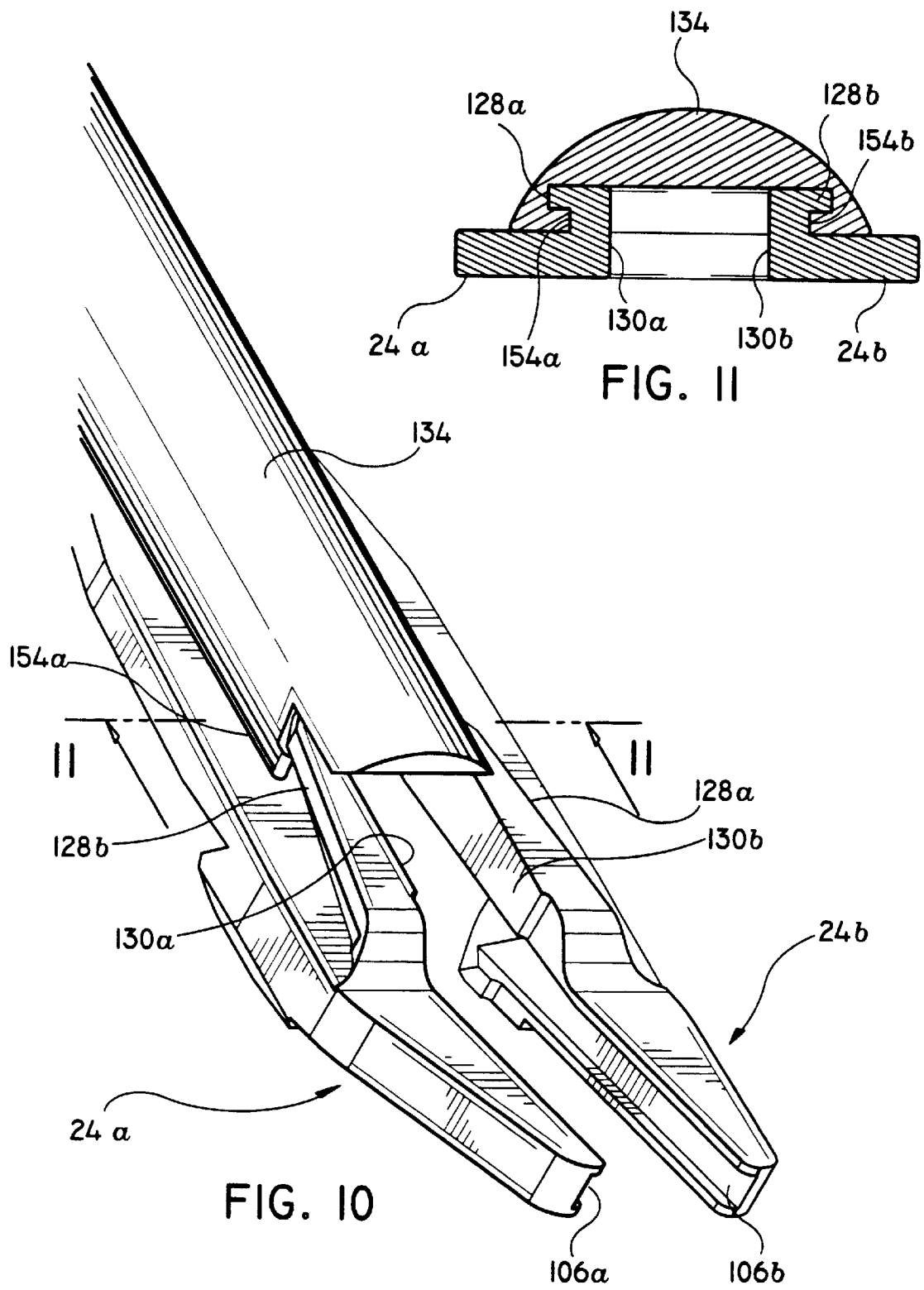

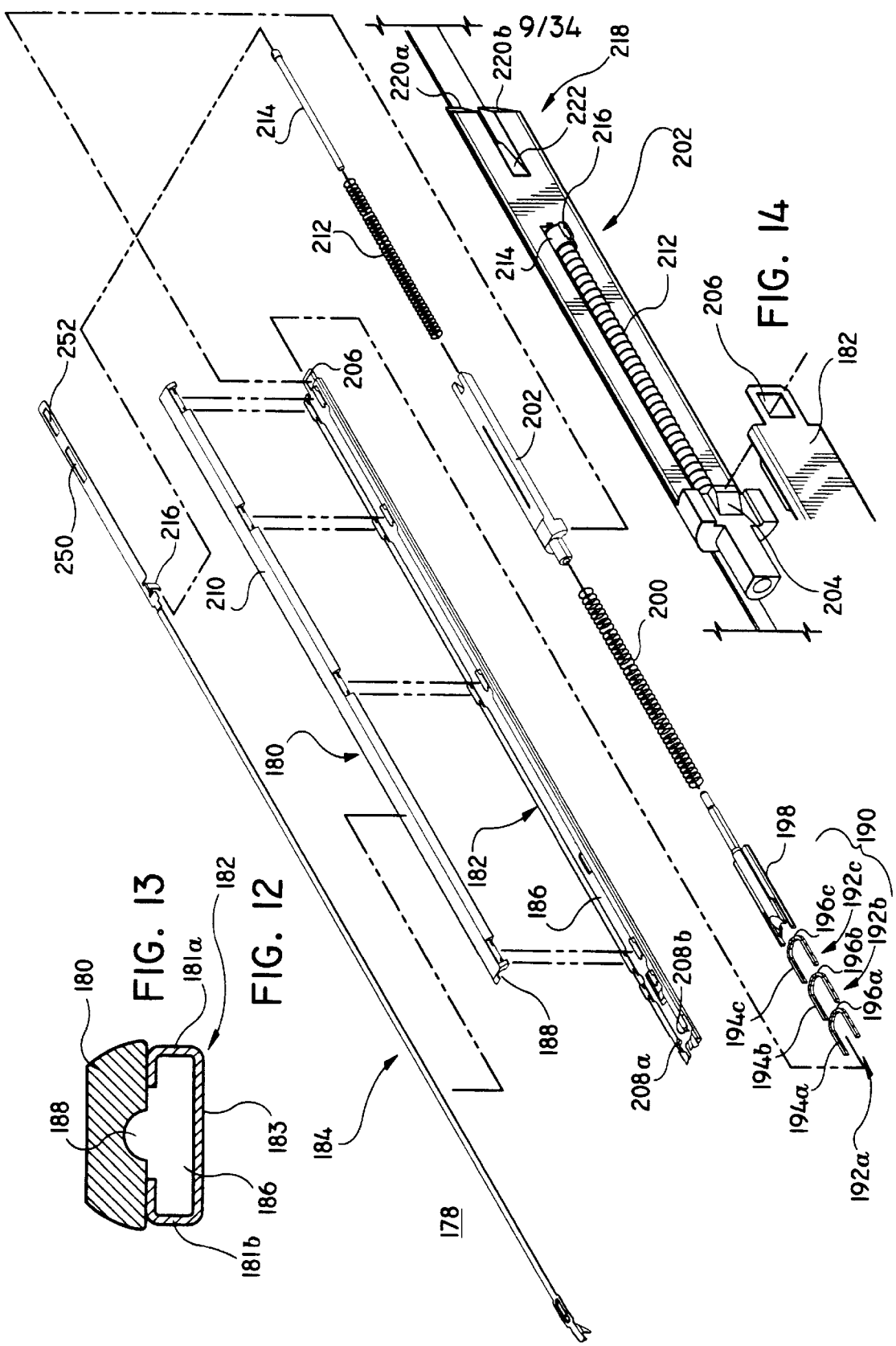

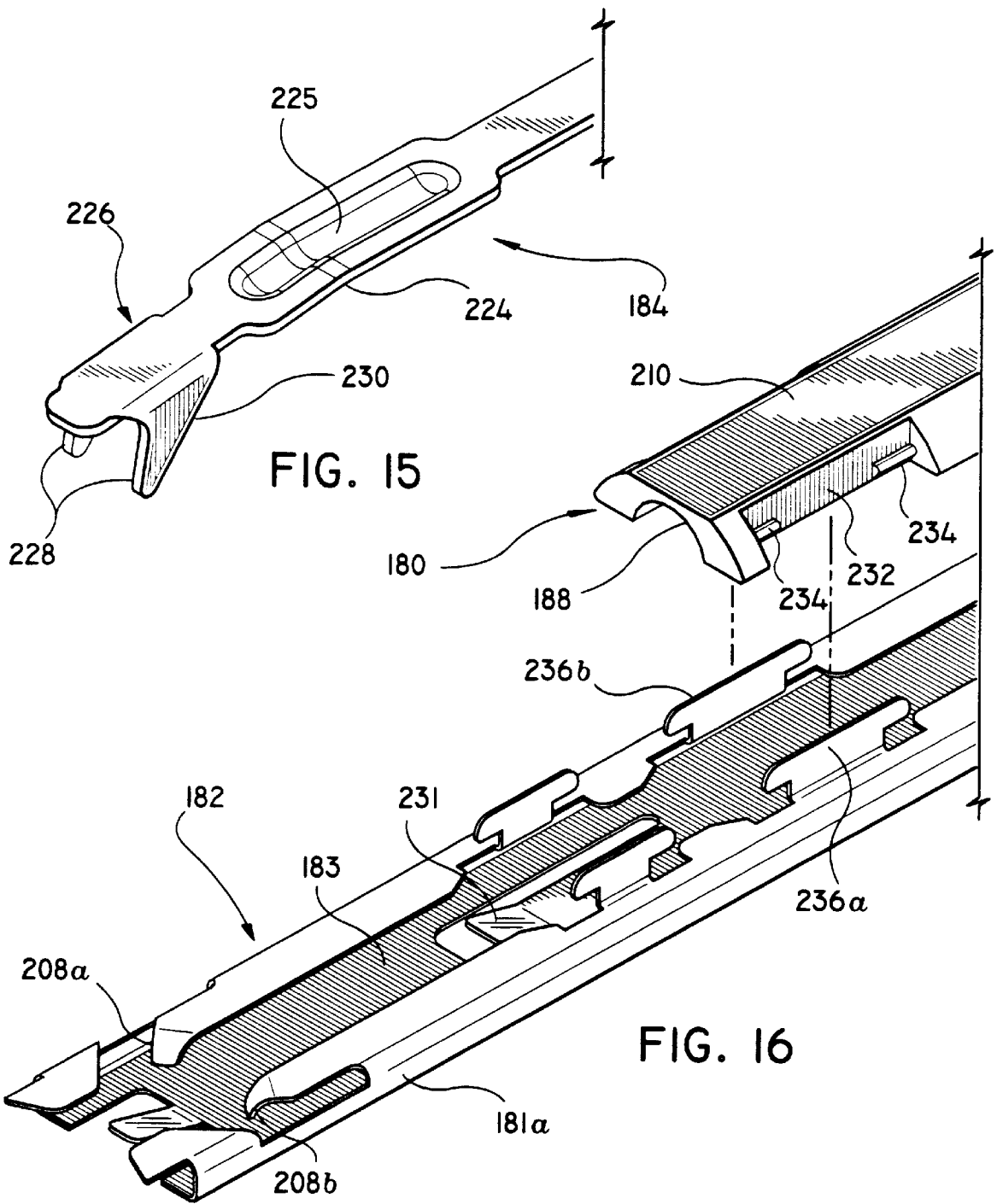

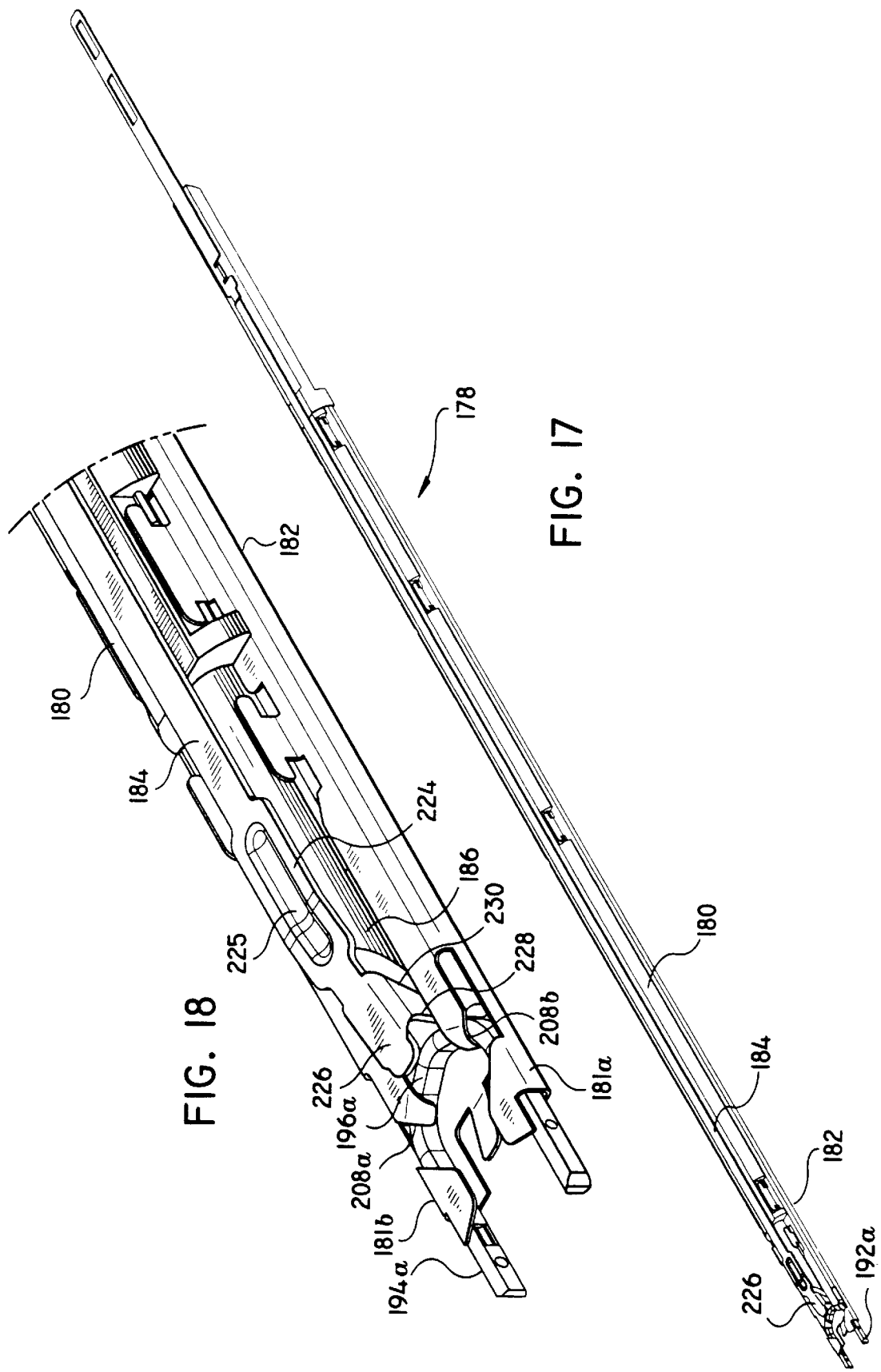

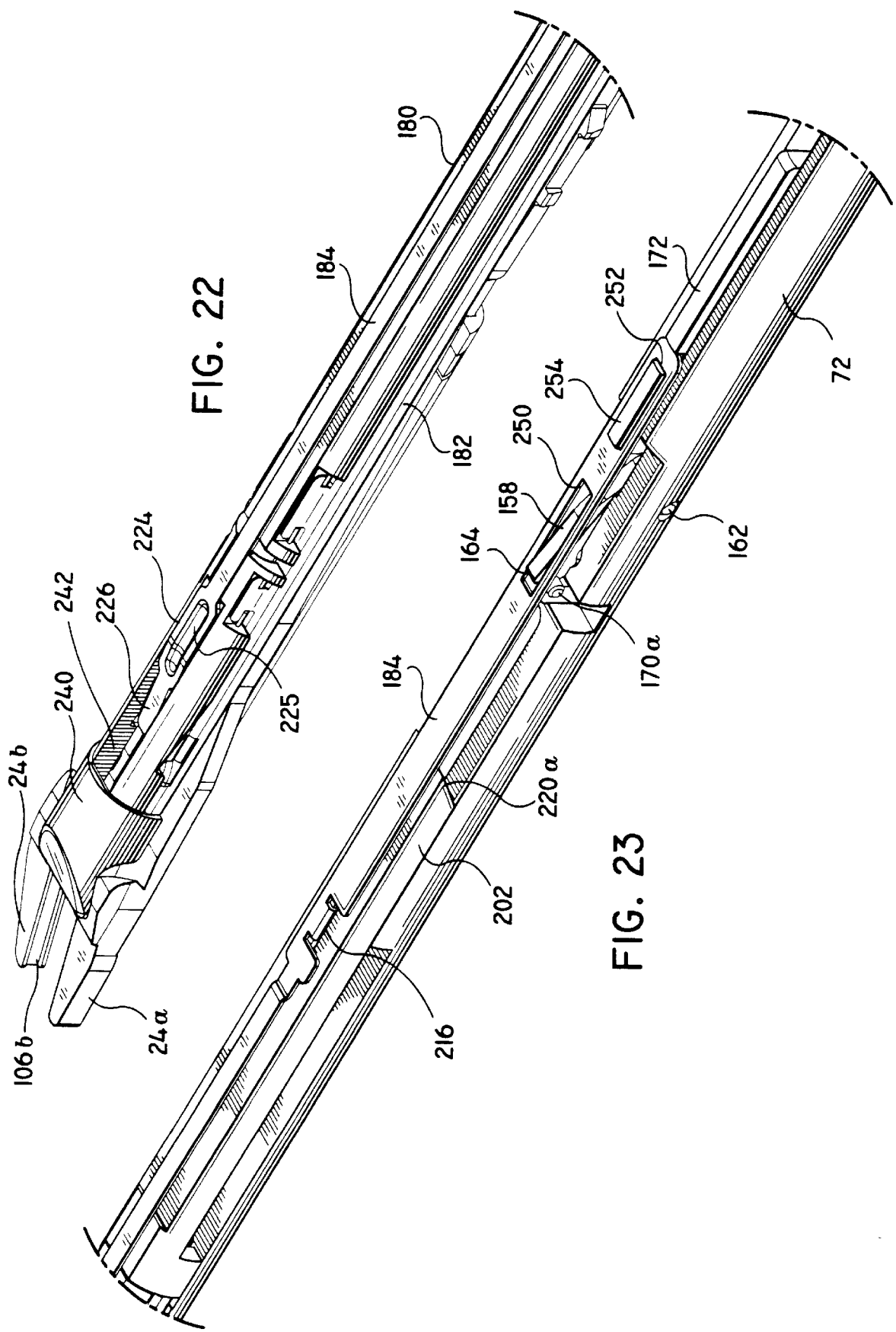

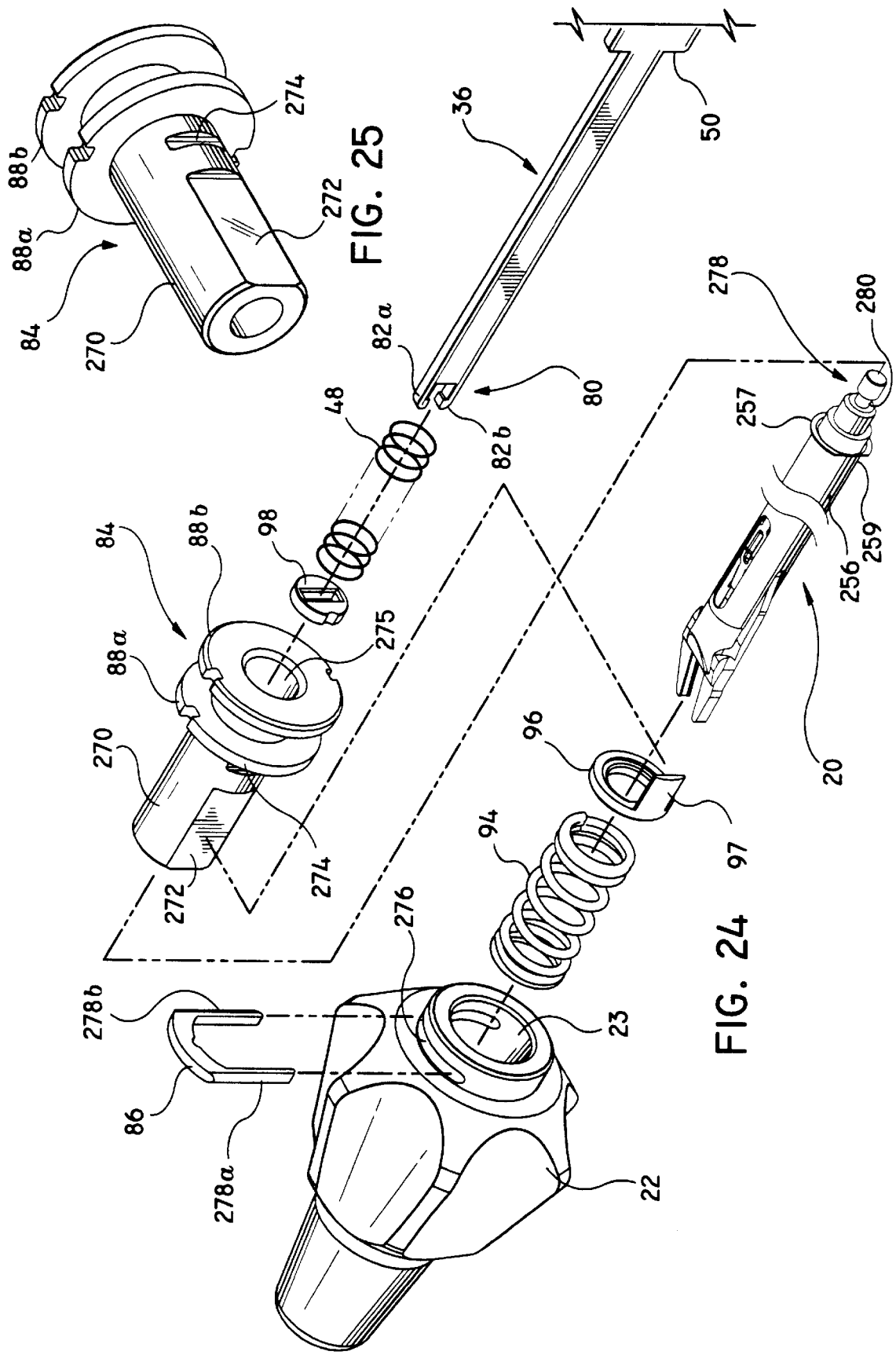

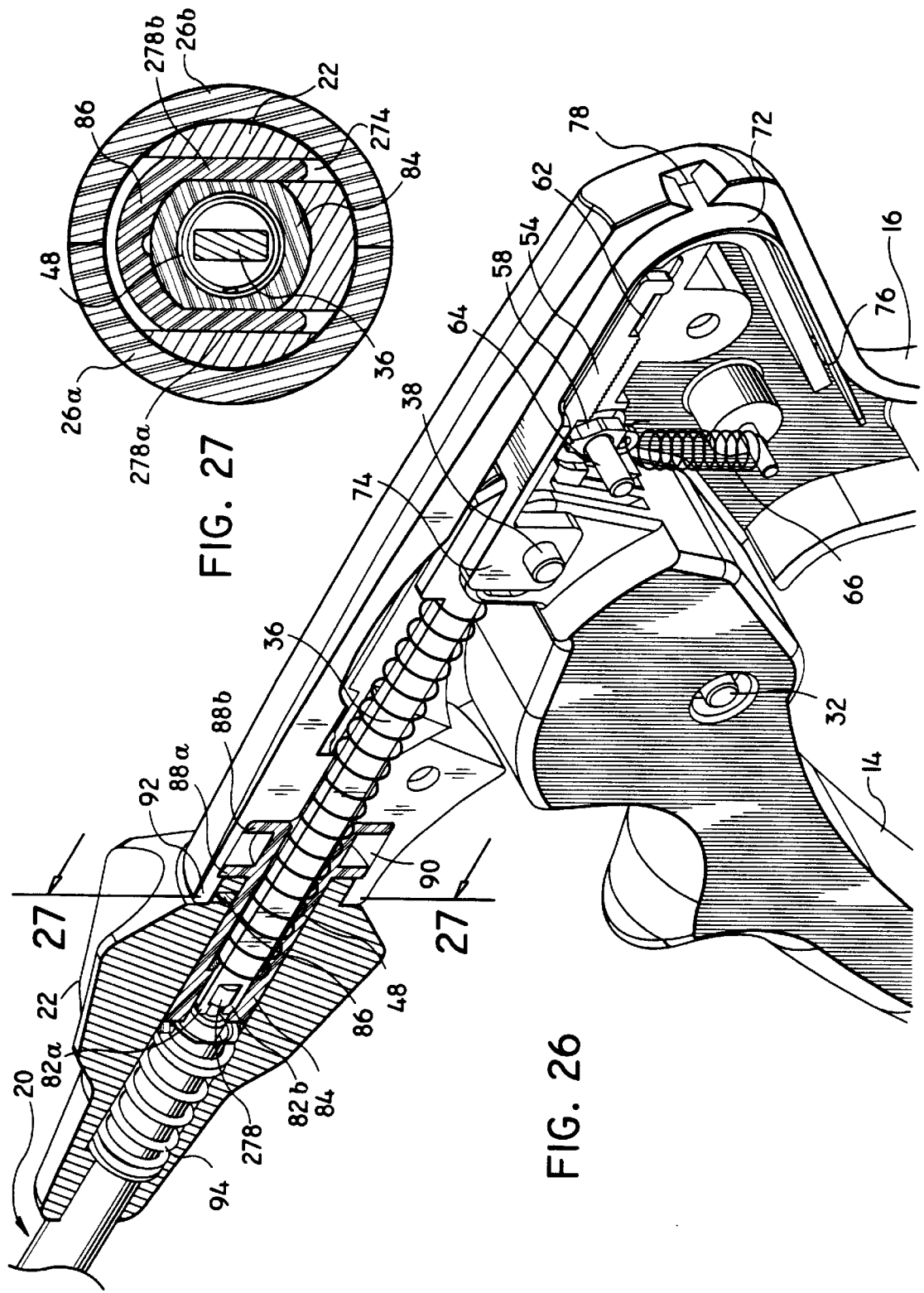

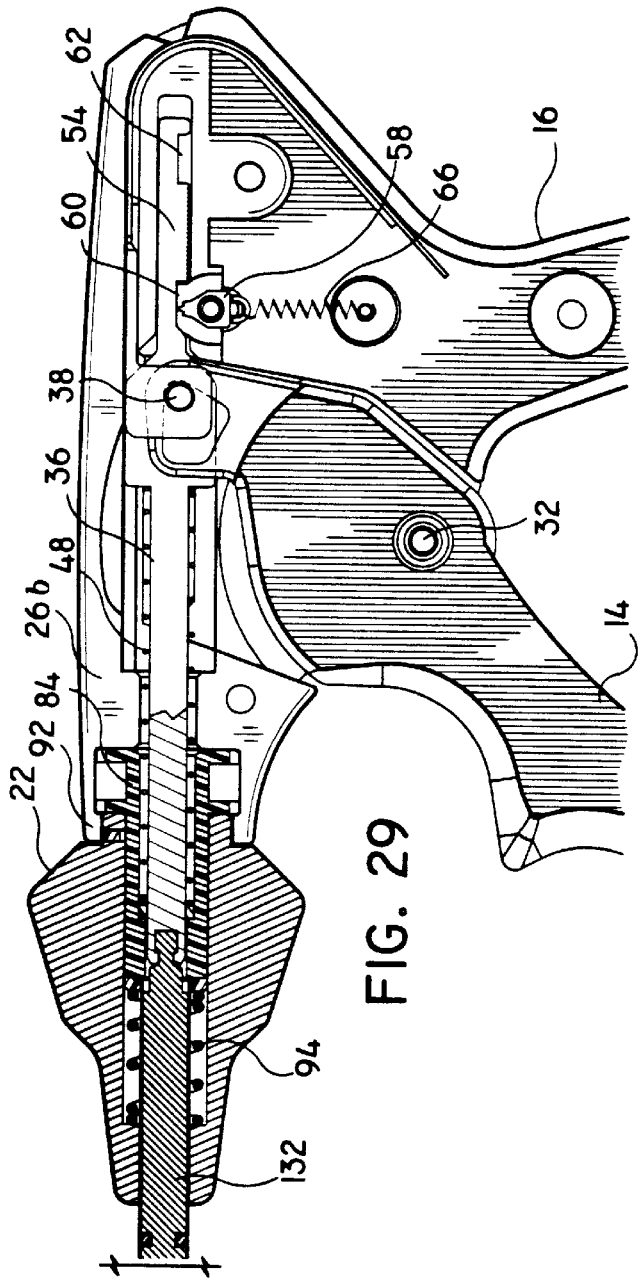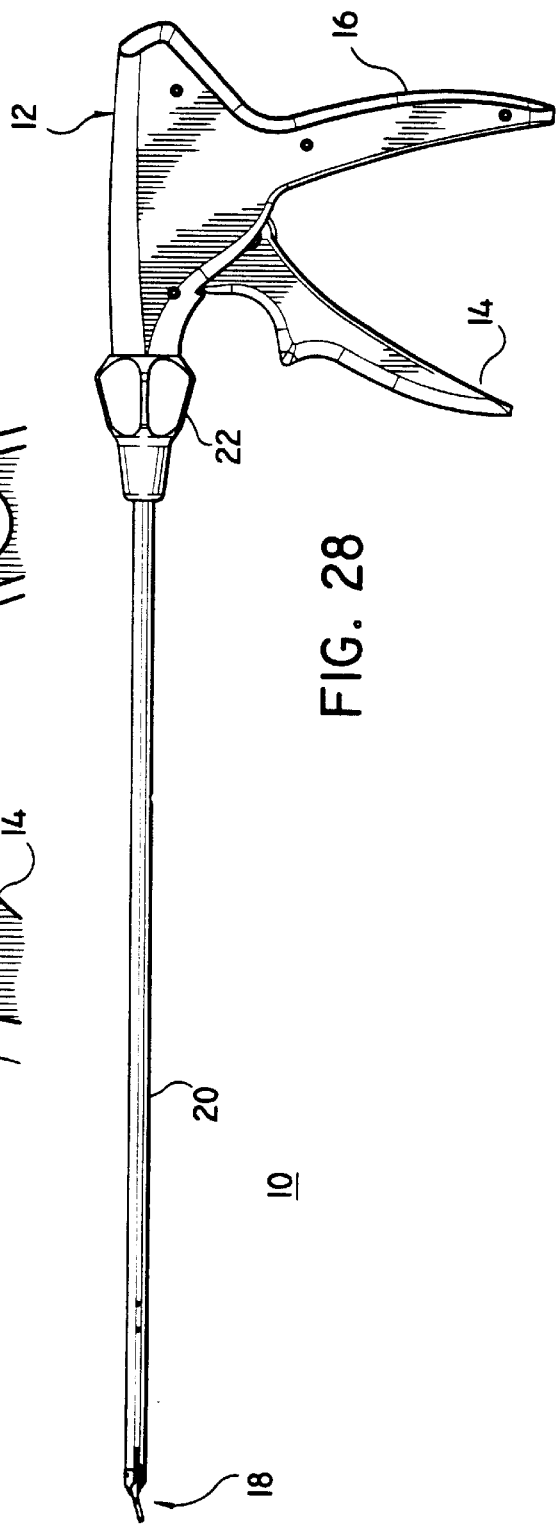

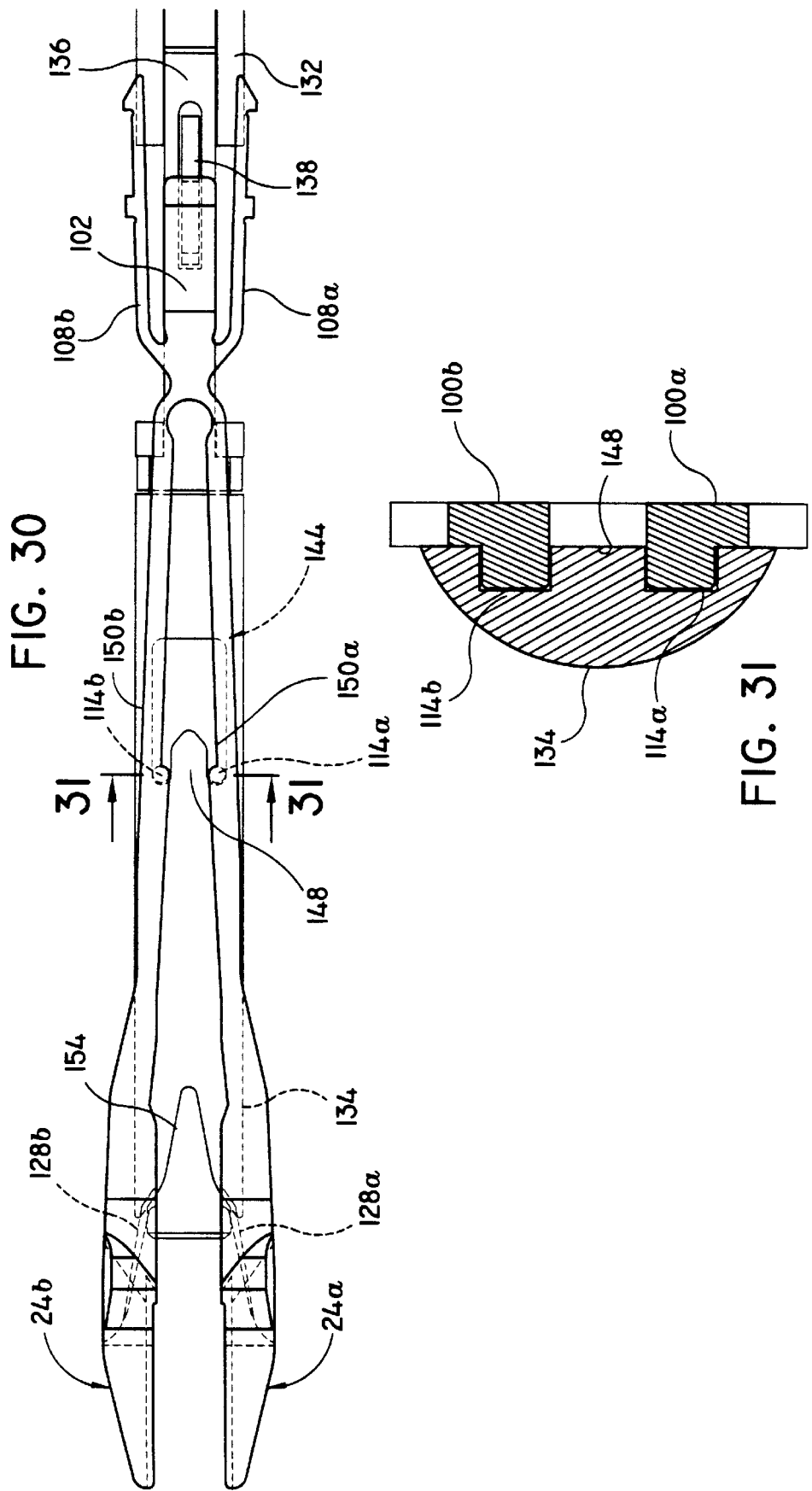

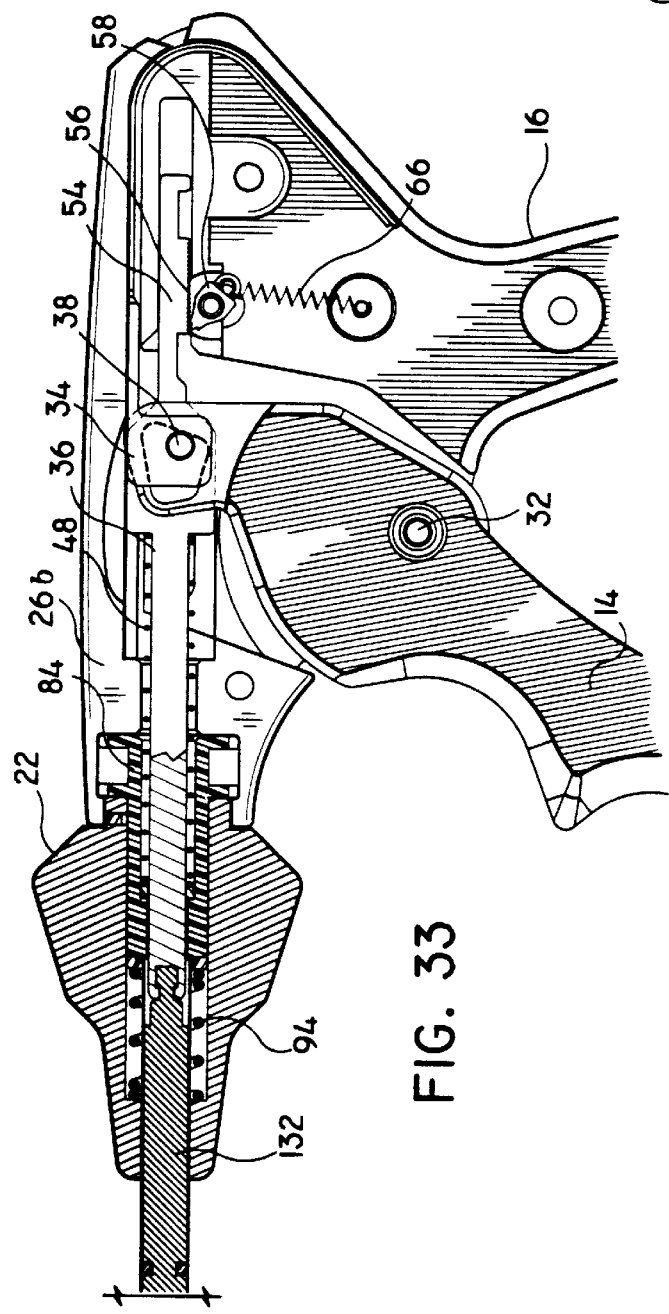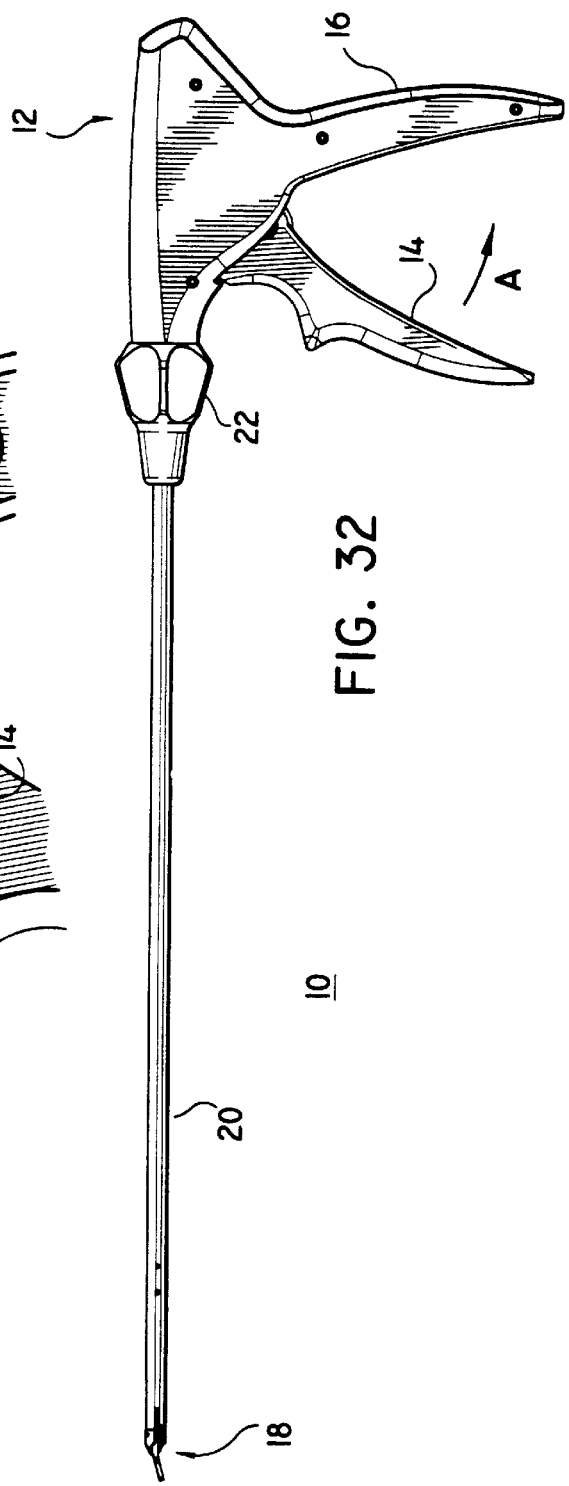

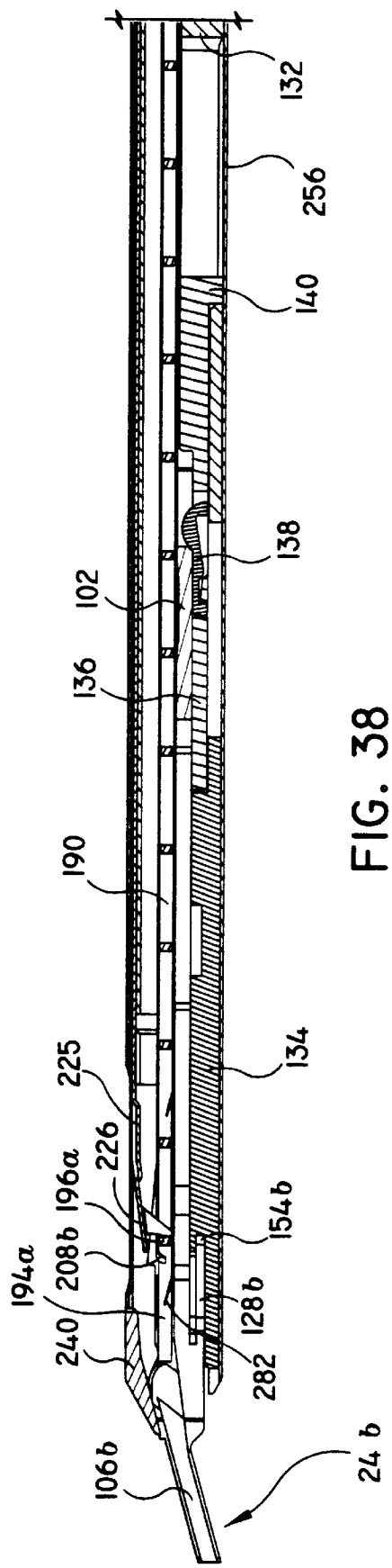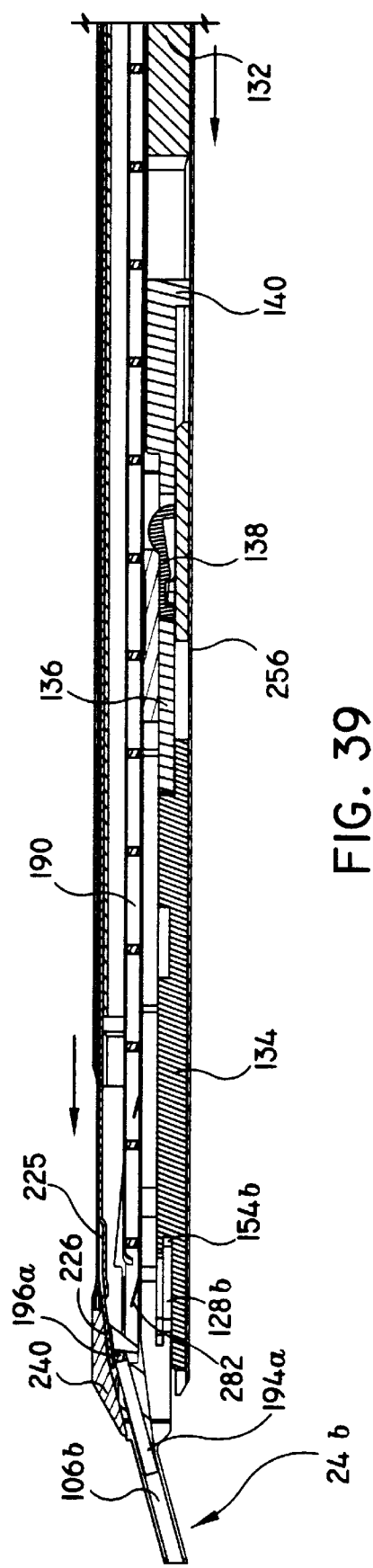
FIG. 38
FIG. 39

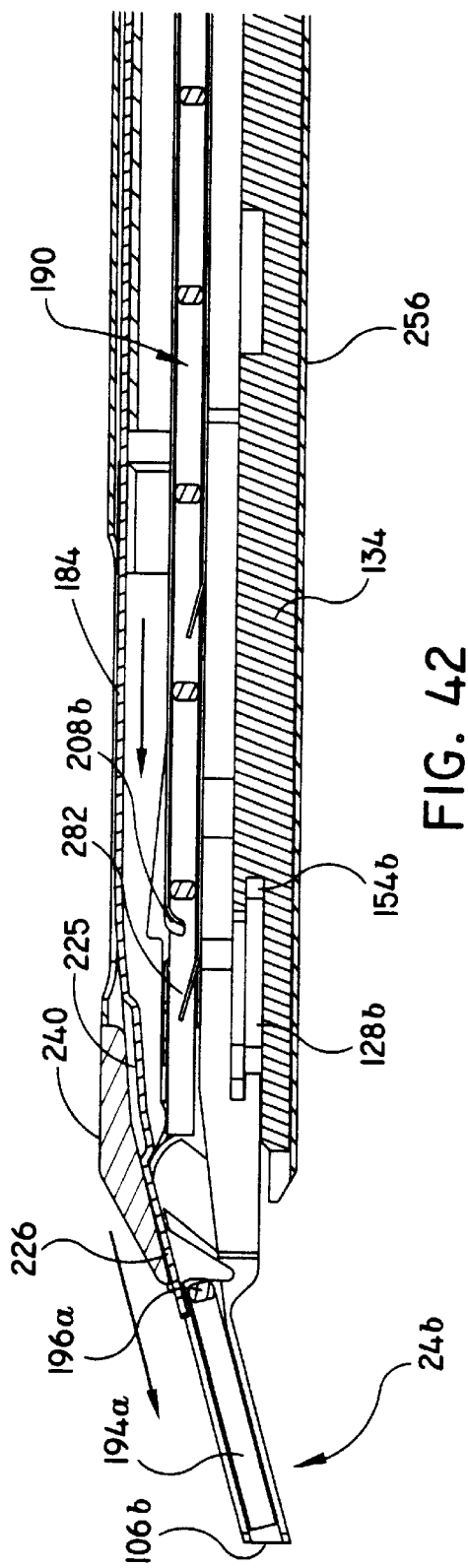
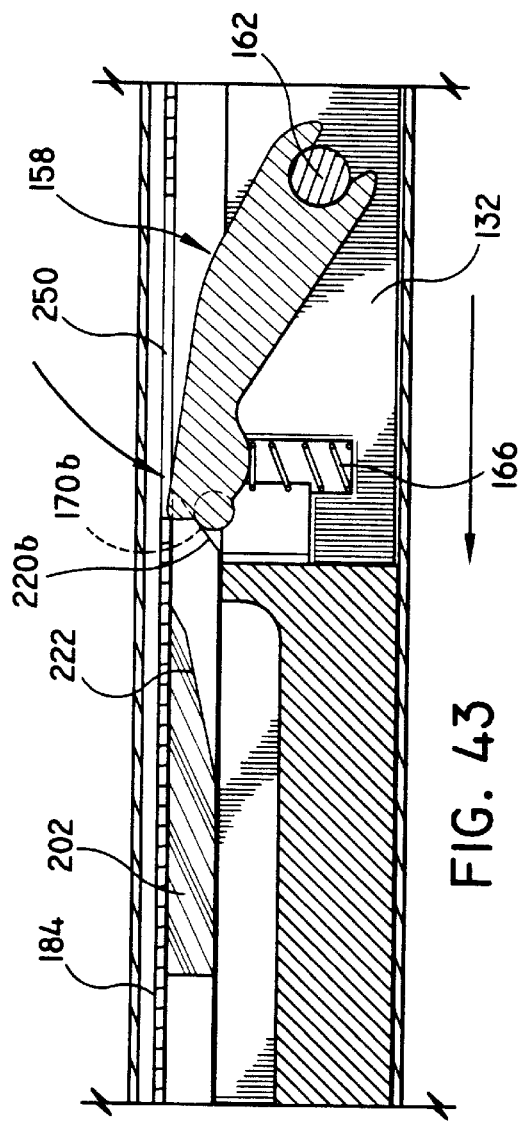

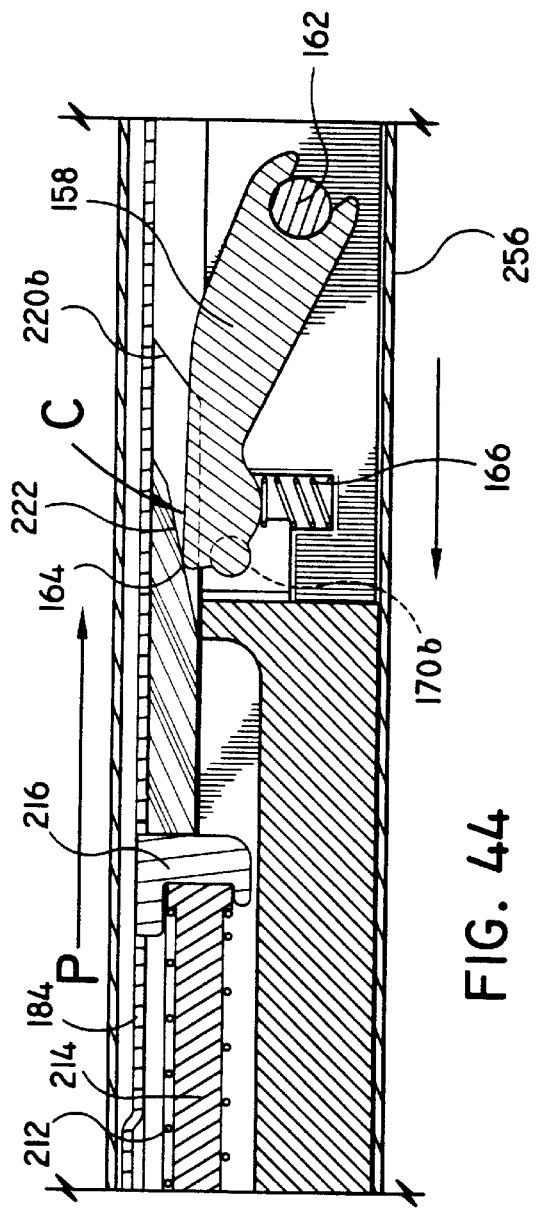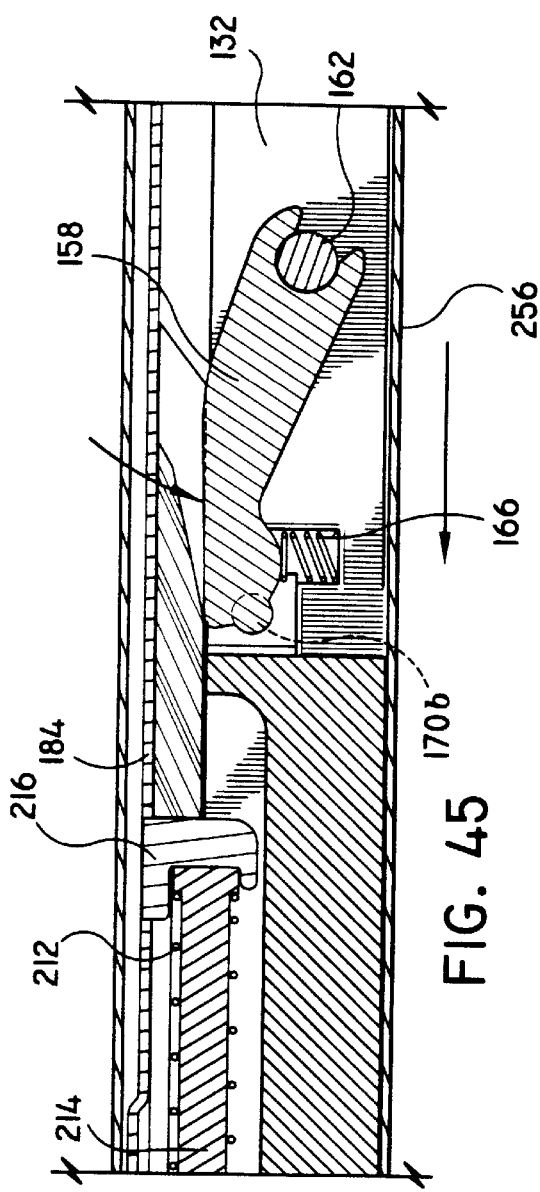

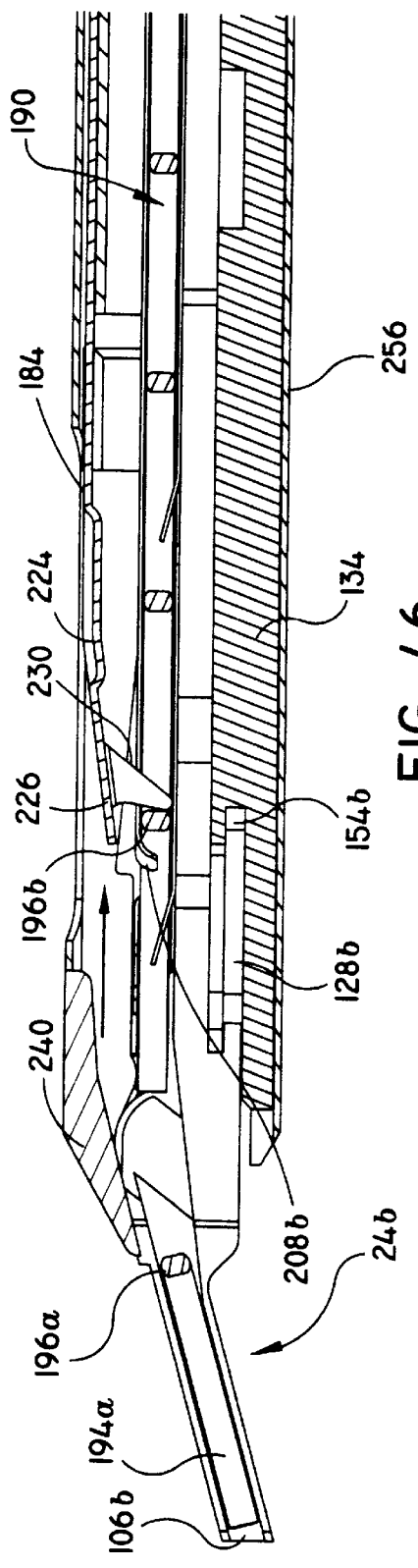
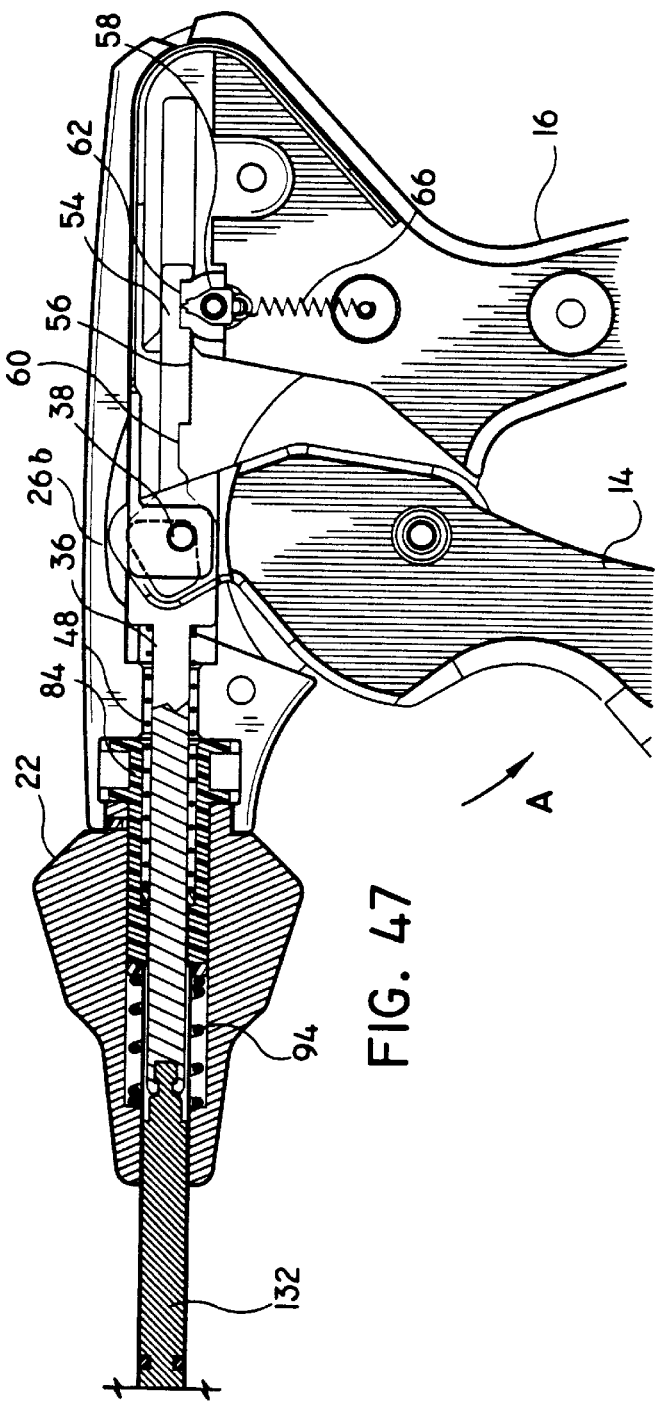
FIG. 46
FIG. 47

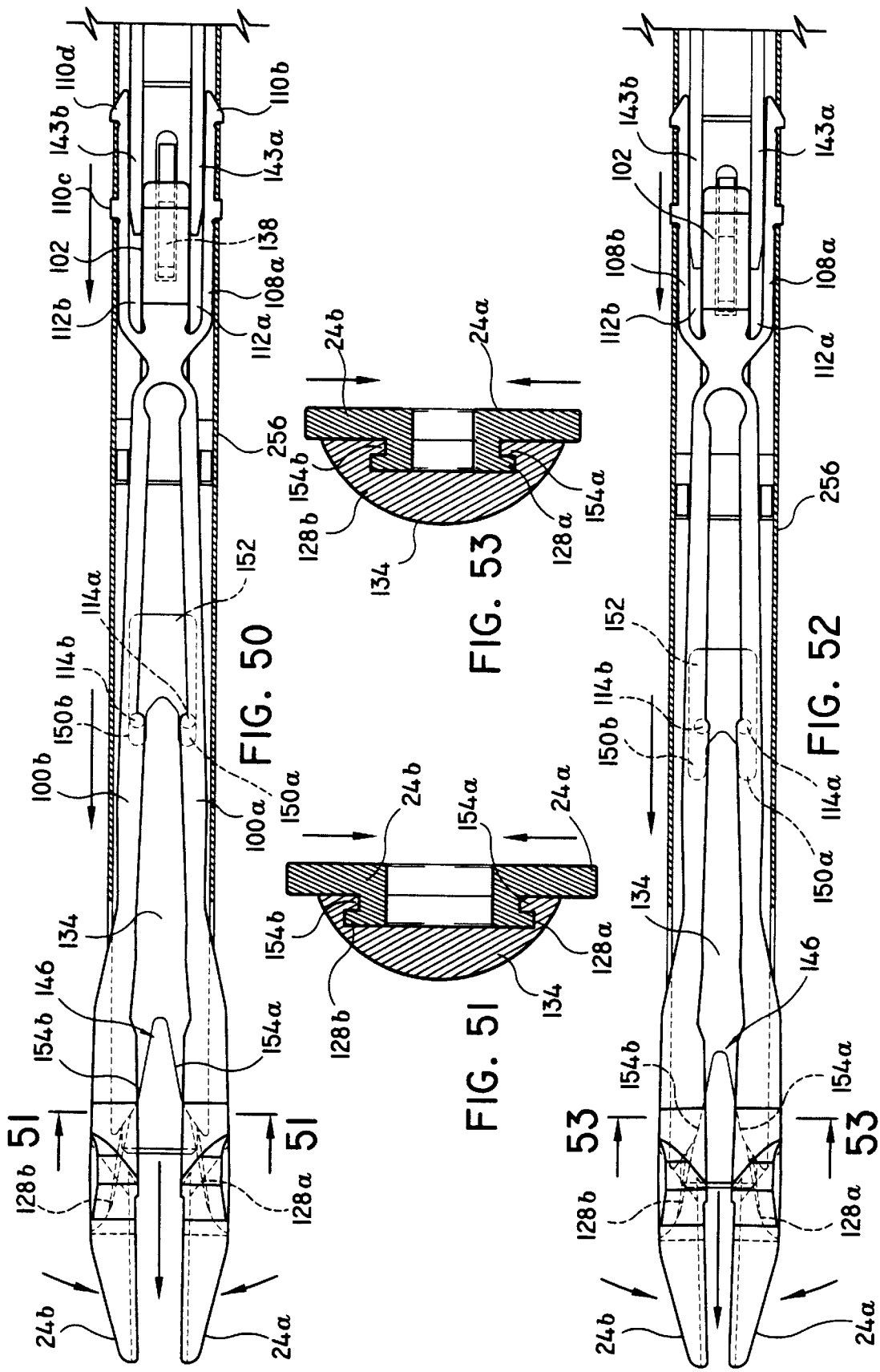

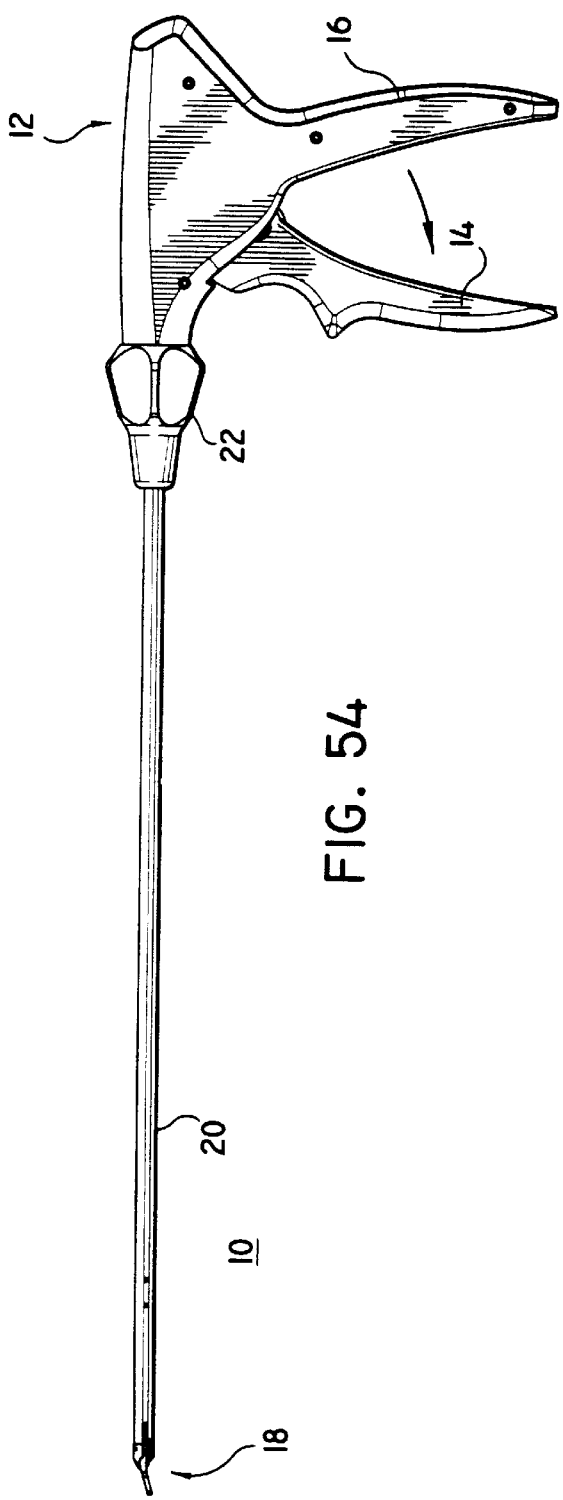
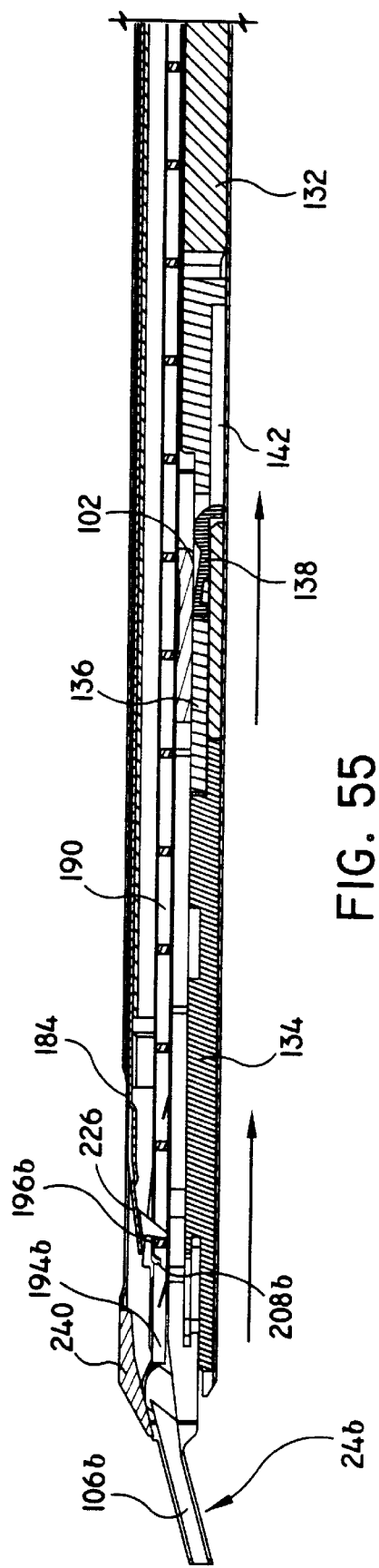
FIG. 54
FIG. 55

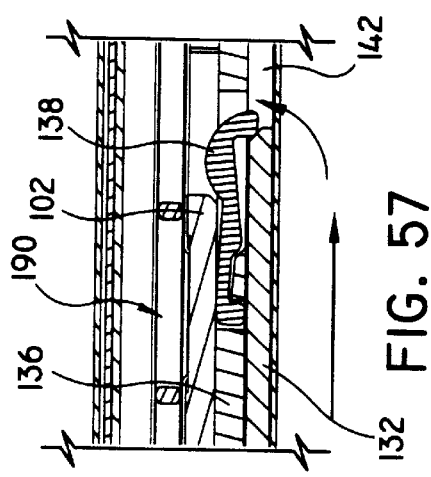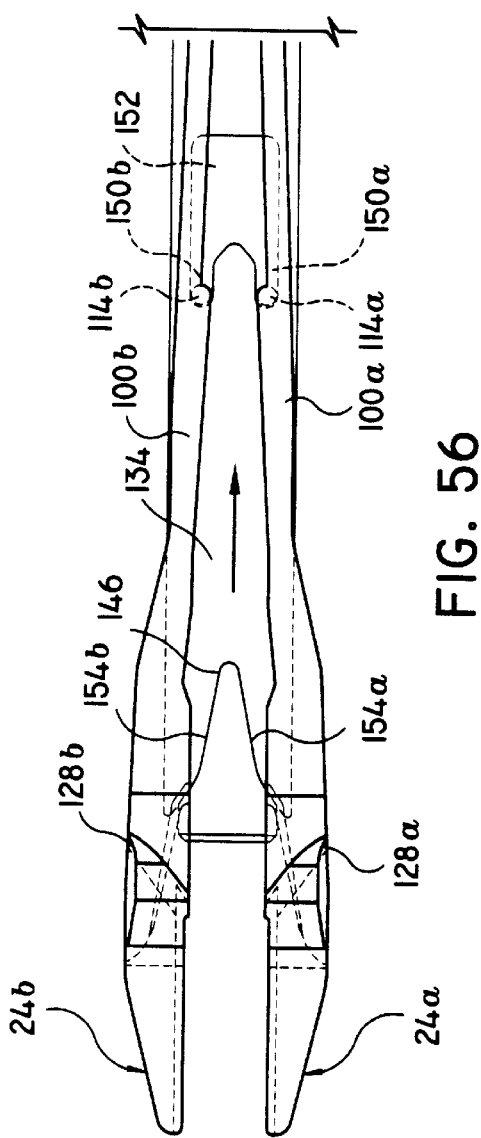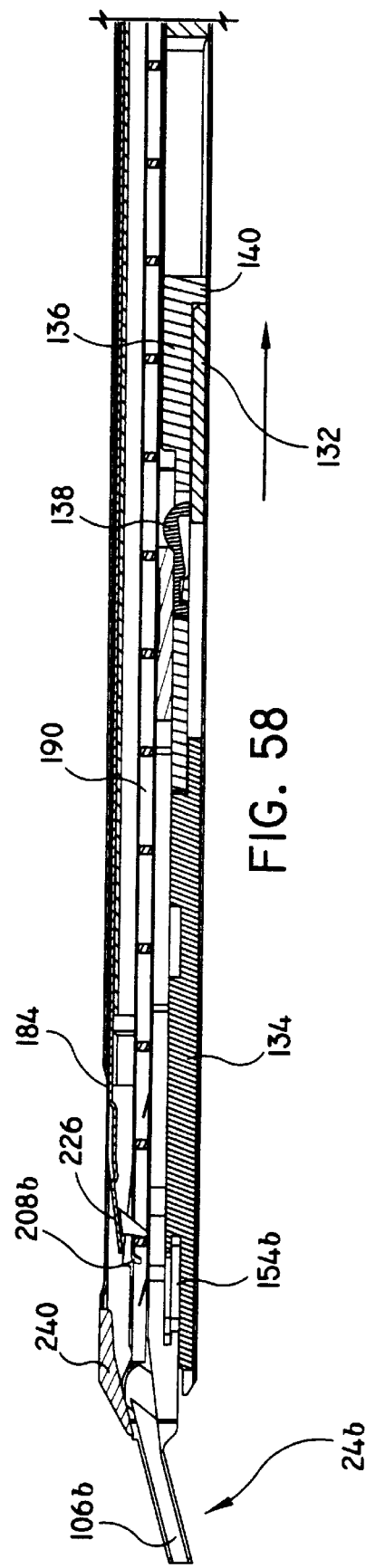

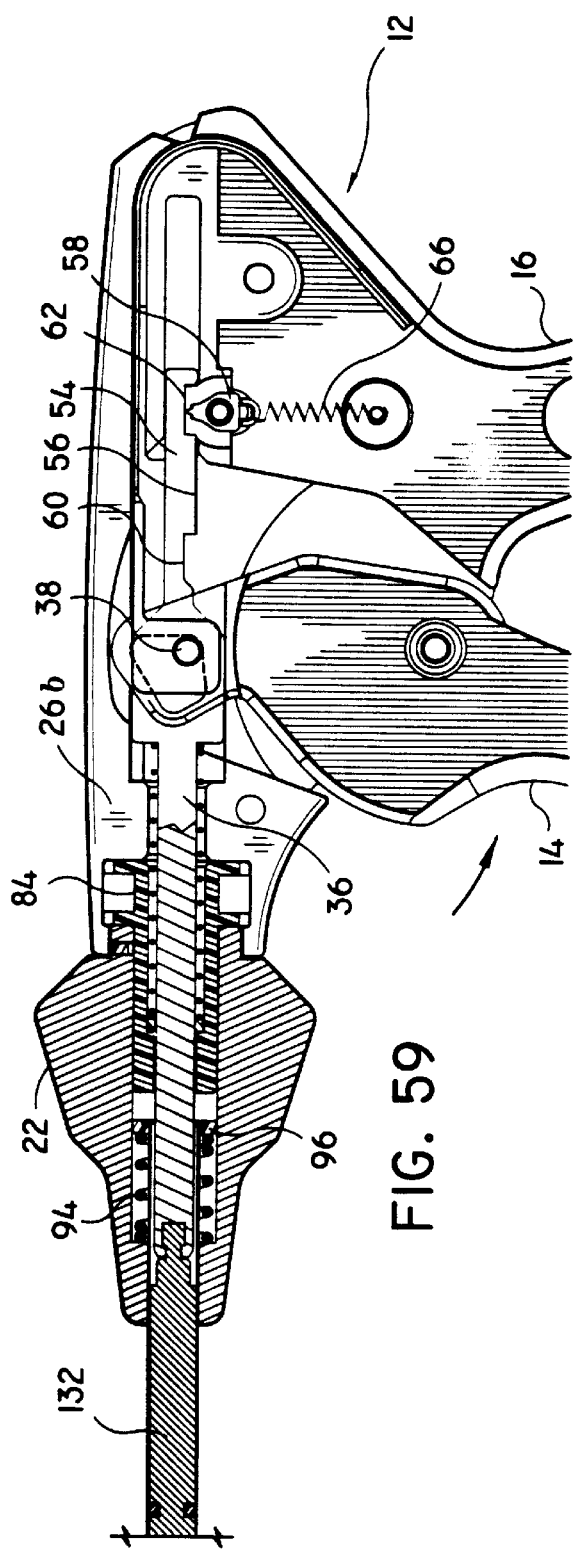
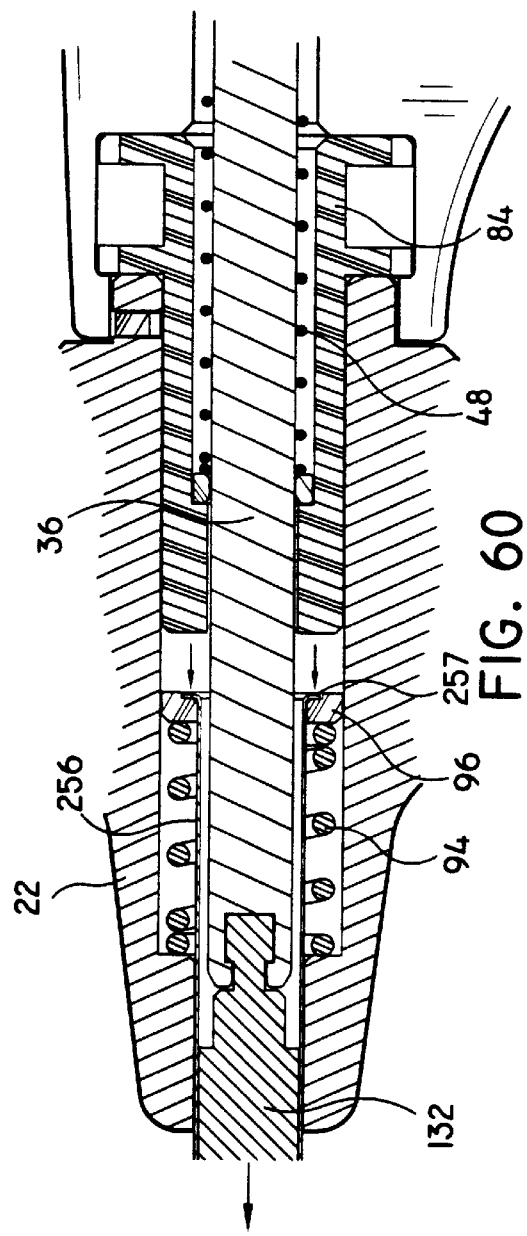

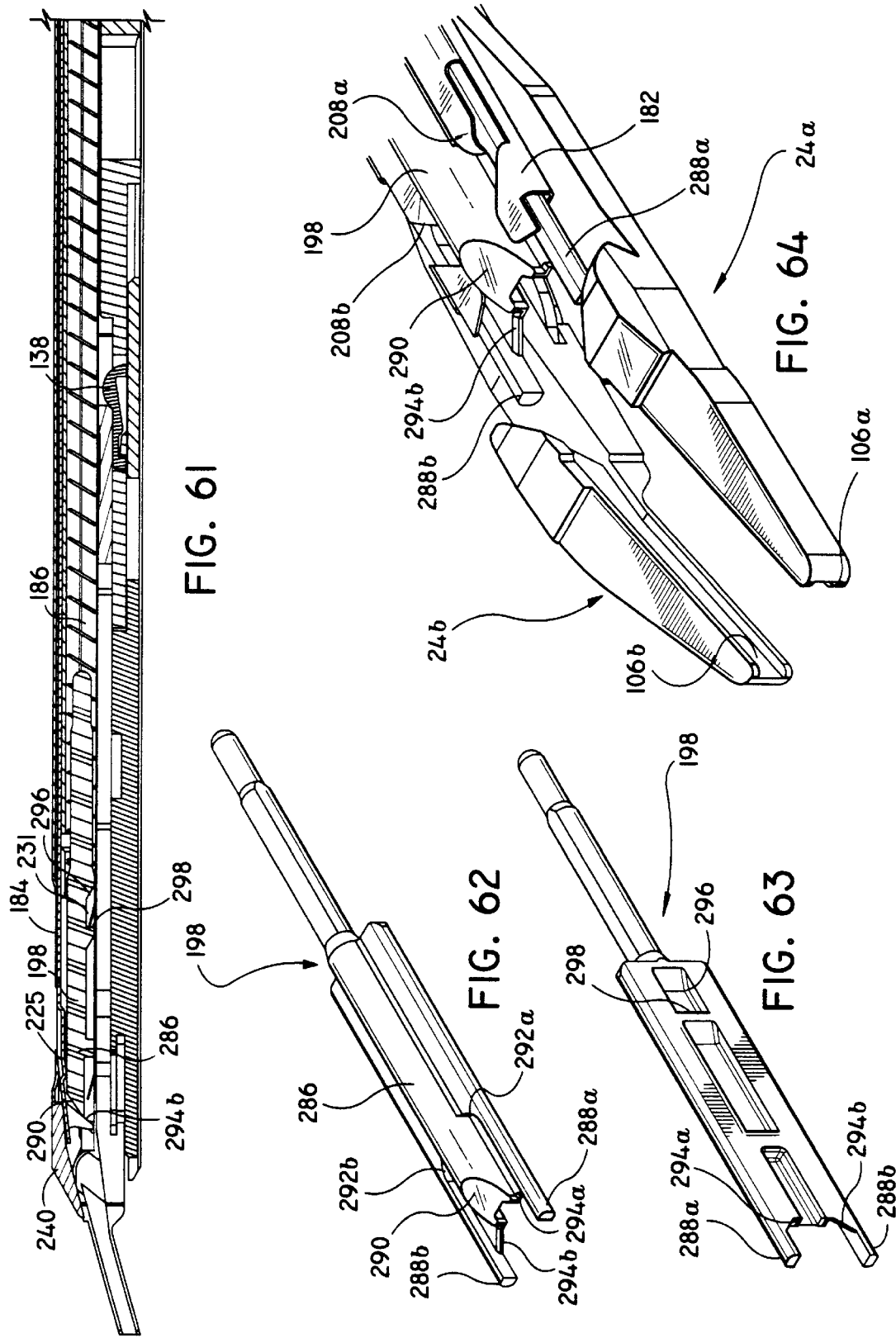

APPARATUS FOR APPLYING SURGICAL CLIPS

BACKGROUND OF THE INVENTION

1. Technical Field

The present disclosure relates to apparatus for applying surgical clips to body tissue. In particular, the disclosure relates to surgical clip appliers configured to be inserted through relatively narrow access devices such as those used in laparoscopic or endoscopic procedures.

2. Description of the Related Art

Laparoscopic procedures are performed in the interior of the abdomen through a small incision, e.g., through narrow endoscopic tubes or cannulas inserted through a small entrance incision in the skin. Minimally invasive procedures performed elsewhere in the body are often generally referred to as "endoscopic" procedures. Typically in such procedures, a tube or cannula device is extended into the patient's body through the entrance incision to provide an access port which allows insertion of various surgical instruments therethrough. These instruments are used for performing surgical procedures on organs, blood vessels, ducts, or body tissue far removed from the incision. Often during these procedures, it is necessary to apply hemostatic clips to blood vessels or various ducts to prevent the flow of body fluids therethrough during the procedure.

Multiple endoscopic clip appliers (i.e., clip appliers that are able to apply multiple clips in endoscopic or laparoscopic procedures during a single entry into the body cavity) are described in commonly-assigned U.S. Pat. Nos. 5,084,057 and 5,100,420 to Green et al., the disclosures of which are hereby incorporated by reference herein. Other multiple endoscopic clip appliers are disclosed in commonly-assigned copending U.S. patent application Ser. Nos. 08/134,347, filed Oct. 8, 1993 by Pratt et al., 08/515,341, filed Aug. 15, 1995 by Pier et al., and 08/546,430 filed Oct. 20, 1995 by Whitfield et al., the contents of which are also hereby incorporated by reference herein.

One advantage of minimally invasive surgical procedures is the reduction of trauma to the patient as a result of accessing internal organs through smaller incisions. Known multiple endoscopic clip appliers have greatly facilitated the advent of more advanced minimally invasive procedures by permitting multiple clip applications during a single entry into the body cavity. Commercially available multiple endoscopic clip appliers are generally of 10 mm outer diameter and are adapted to be introduced through a 10 mm cannula. As minimally invasive procedures continue to evolve and the advantages thereof are extended to additional clinical applications, it has become desirable to further reduce incision size(s) and therefore the size of all instrumentation introduced therethrough.

The structure of surgical instruments intended to perform numerous functions within a confined space is necessarily complex. Consequently, the assembly process for these instruments is often complicated and may involve numerous relatively small parts.

It is therefore desirable to maximize the ease with which such instruments may be assembled.

It is also desirable to provide a multiple endoscopic clip applier having structure which facilitates the application of surgical clips while further minimizing the required incision size at the surgical site.

SUMMARY

A surgical clip applying instrument is disclosed which includes a handle portion, a body extending distally from the handle portion and defining a longitudinal axis, and a plurality of surgical clips disposed within the body. A jaw assembly is mounted adjacent a distal end portion of the body. The jaw assembly includes first and second jaw portions movable between a spaced-apart and an approximated position. A clip pusher is provided to individually distally advance a distalmost surgical clip to the jaw assembly while the jaw portions are in the spaced-apart position. An actuator at least partially disposed within the body is longitudinally movable in response to actuation of the handle portion. A jaw closure member is positioned adjacent the first and second jaw portions to move the jaw portions to the approximated position. The actuator and the jaw closure member define an interlock therebetween to produce simultaneous movement of the actuator and the jaw closure member when the actuator is positioned adjacent the distal end portion of the body.

BRIEF DESCRIPTION OF THE DRAWINGS

Various embodiments of the subject surgical apparatus are described herein with reference to the drawings wherein:

FIG. 3 is an enlarged side view of the handle portion of the subject surgical clip applier, illustrating a preferred ratchet assembly;

FIG. 4 is an enlarged perspective view of a preferred jaw assembly of the subject surgical clip applier;

FIG. 4A is an enlarged perspective view of the jaw assembly, illustrating position tabs formed on shank portions thereof;

FIG. 7 is a perspective view with parts separated of a preferred spindle subassembly;

FIG. 7A is an enlarged perspective view of the trip lever;

FIG. 8 is an enlarged perspective view of the linkage structure allowing selective interlocking between the spindle and the driver;

FIG. 9 is an enlarged perspective view of camming structures formed in the distal end portion of the driver;

FIG. 10 is an enlarged perspective view from below, illustrating the camming interaction of the driver with the jaw assembly;

FIG. 11 is a cross-sectional view of the driver and the jaw assembly, taken along line 11—11 of FIG. 10;

FIG. 12 is a perspective view with parts separated of a preferred clip advancement subassembly;

FIG. 13 is an enlarged cross-sectional view of a feed chute formed by the attachment of the upper housing and the lower housing;

FIG. 14 is an enlarged perspective view of the attachment of the mounting block with the lower housing;

FIG. 15 is an enlarged perspective view of the distal end of the thrust bar;

FIG. 16 is an enlarged perspective view of the attachment of the upper housing with the lower housing;

FIG. 17 is a perspective view of a preferred clip advancement subassembly;

FIG. 18 is an enlarged perspective view of the distal end portion of the clip advancement subassembly, illustrating the lower housing, the upper housing, the thrust bar, and a surgical clip;

FIG. 22 is an enlarged perspective view of the distal end portion of the instrument with the outer sleeve removed;

FIG. 23 is an enlarged perspective view of the endoscopic portion, illustrating an interlocking mechanism between the thrust bar and the spindle;

FIG. 24 is a perspective view with parts separated of the rotation knob assembly;

FIG. 25 is an enlarged perspective view of the bushing shown in FIG. 24;

FIG. 26 is an enlarged perspective view in partial cross-section illustrating the junction of the handle portion and the endoscopic portion;

FIG. 27 is a cross-sectional view taken along line 27—27 of FIG. 26;

FIG. 28 is a side view of the subject surgical clip applier, illustrating a movable handle in the open position;

FIG. 29 is an enlarged cross-sectional view of the handle portion in the open position of FIG. 28;

FIG. 30 is a plan view from above illustrating the relative position of the jaw assembly and the driver when the position tabs are disposed at the distal end of the camming structure;

FIG. 31 is an enlarged cross-sectional view taken along line 31—31 of FIG. 30, illustrating the position tabs disposed in the camming structure;

FIG. 32 is a side view of the subject surgical clip applier, illustrating the movable handle at the beginning of the closing stroke;

FIG. 33 is an enlarged cross-sectional view of the handle portion of the instrument in the progressive actuation position of FIG. 32;

FIG. 38 is an enlarged cross-sectional view of the endoscopic portion, illustrating the thrust bar contacting a distalmost clip;

FIG. 39 is an enlarged cross-sectional view of the endoscopic portion, illustrating the advancement of a surgical clip into the jaw portions of the instrument in the progressive actuation position of FIG. 32;

FIG. 42 is an enlarged cross-sectional view of the jaw assembly, illustrating the thrust bar advancing a surgical clip to the jaw portions of the instrument in the actuation position of FIG. 40;

FIG. 43 is an enlarged cross-sectional view of the endoscopic portion, illustrating the trip lever of the spindle contacting a camming surface on the mounting block;

FIG. 44 is an enlarged cross-sectional view of the endoscopic portion, illustrating the trip lever pivoting out of engagement with the thrust bar and the thrust bar moving proximally;

FIG. 45 is an enlarged cross-sectional view of the endoscopic portion, illustrating further pivoting of trip lever;

FIG. 46 is an enlarged cross-sectional view of the jaw assembly, illustrating proximal movement of the thrust bar over the crown portion of the next surgical clip positioned in the feed chute;

FIG. 47 is an enlarged cross-sectional view of the handle portion with the movable handle in the final throw of the closing stroke;

FIG. 50 is a plan view from below, illustrating the relative position of the jaw assembly and the driver as camming surfaces on the driver begin to approximate the jaw portions;

FIG. 51 is an enlarged cross-sectional view taken along line 51—51 of FIG. 50, illustrating camming surfaces of the jaw assembly and the driver;

FIG. 52 is a plan view from below, illustrating the relative positions of the jaw assembly and the driver as camming surfaces on the thrust bar approximate the jaw portions;

FIG. 53 is an enlarged cross-sectional view taken along line 5—53 of FIG. 52, illustrating camming surfaces of the jaw assembly and the driver;

FIG. 54 is a side view, illustrating the movable handle returning to an open position;

FIG. 55 is an enlarged cross-sectional view of the endoscopic portion, illustrating the driver and the spindle interlocked and returning proximally;

FIG. 56 is a plan view illustrating the driver moving proximally with respect to the jaw assembly;

FIG. 57 is an enlarged cross-sectional view of the endoscopic portion, illustrating the detent spring pivoting upward out of engagement with the spindle;

FIG. 58 is an enlarged cross-sectional view of the endoscopic portion, illustrating the spindle returning proximally and the driver remaining stationary;

FIG. 59 is an enlarged cross-sectional view of the handle portion with the movable handle in the final throw of the closing stroke;

FIG. 60 is an enlarged cross-sectional view, illustrating the release mechanism;

FIG. 61 is a cross-sectional view of the endoscopic portion, illustrating the clip follower in a distalmost position;

FIG. 62 is an enlarged perspective view of the clip follower;

FIG. 63 is an enlarged perspective view from below of the clip follower;

FIG. 64 is an enlarged perspective view of the clip follower adjacent the jaw subassembly;

DETAILED DESCRIPTION OF PREFERRED EMBODIMENTS

Figure 1:
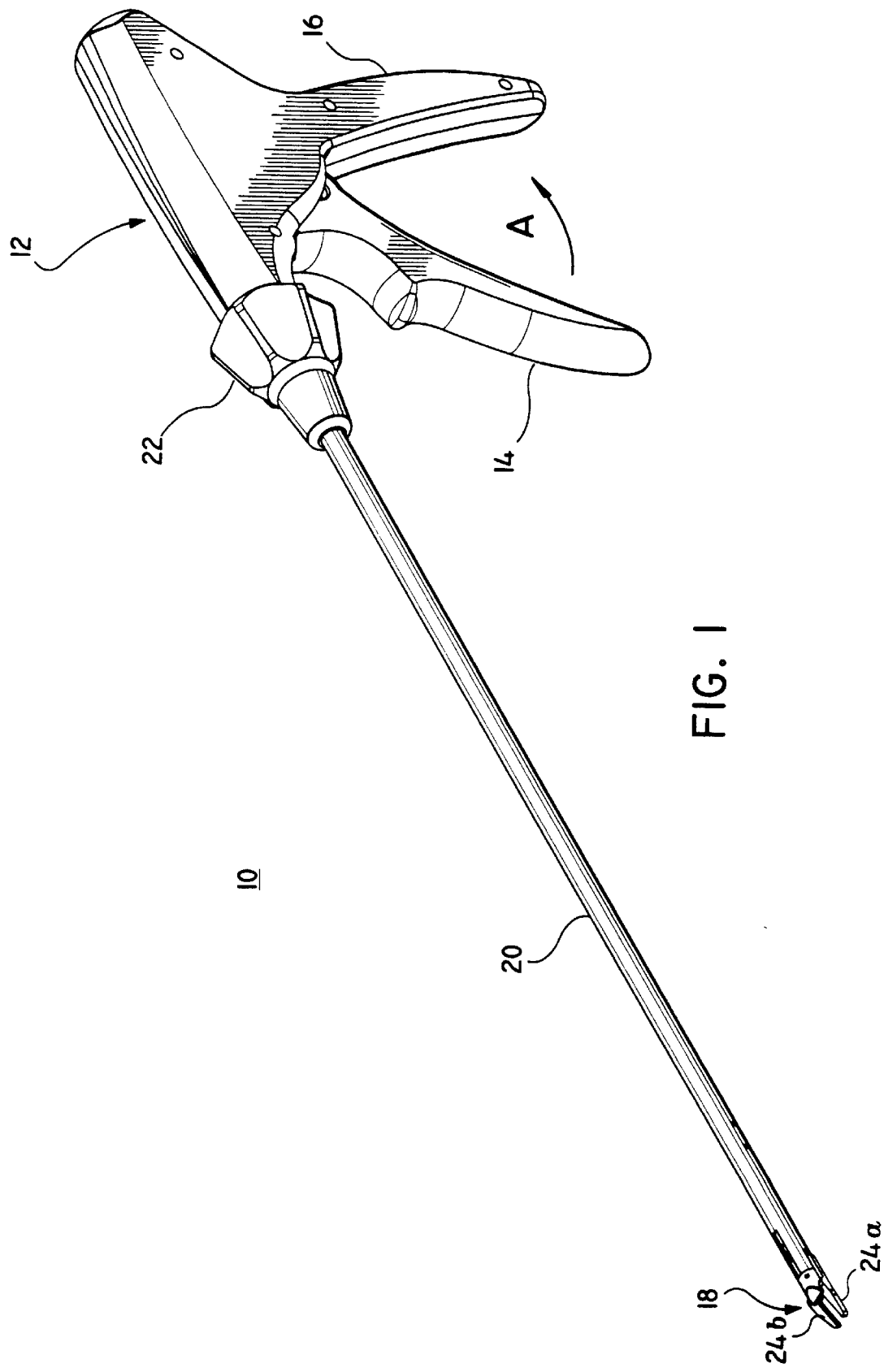
FIG. 1 is a perspective view of a surgical clip applier constructed in accordance with a preferred embodiment of the subject disclosure.

The preferred embodiments of the apparatus disclosed herein will be discussed in terms of endoscopic procedures and apparatus. However, use herein of terms such as "endoscopic" should not be construed to limit the present application to an apparatus for use in conjunction with an endoscopic tube. In addition, it is believed that the present apparatus may find use in laparoscopic or arthroscopic surgery wherein access to the surgical site is achieved through a narrow cannula, or a small incision.

In the drawings and in the description which follows, the term "proximal", as is traditional, will refer to the end of the apparatus which is closest to the operator, while the term "distal" will refer to the end which is furthest from the operator.

Referring now in detail to the drawings in which like reference numerals identify similar or identical elements, a preferred embodiment of the surgical clip applier of the subject disclosure is illustrated in FIG. 1, and is designated generally by reference numeral 10. Clip applier 10 includes handle portion 12 having pivoting or movable handle 14 and stationary handle 16. Manipulation of these handles 14, 16 actuates a tool assembly, such as jaw assembly 18, through elongated body portion 20. The junction at which body portion 20 is joined to handle portion 12 includes fluted rotation collar 22 for remotely varying the angular orientation of jaw assembly 18 relative to the surgical site. Jaw assembly 18 includes first and second juxtaposed jaw portions 24a and 24b, which are simultaneously movable between a substantially approximated configuration in which jaw portions 24a and 24b are in relatively close relation to one another and a spaced configuration in which jaw portions 24a and 24b are separatable at least a sufficient distance to receive an unformed surgical clip therebetween.

With continued reference to FIG. 1, movable handle 14 is shown in a fully open or "at-rest" position with respect to handle 16. Pivoting movement of movable handle 14 with respect to stationary handle 16 in the direction of arrow "A" from the open position to the closed position defines a closing stroke. During this closing stroke, jaw portions 24a and 24b are maintained in the spaced configuration as the distalmost surgical clip is advanced between the spaced apart jaw portions. Further pivoting of movable handle 14 approximates jaw portions 24a and 24b to deform the surgical clip.

Surgical clip applier 10 will now be described with respect to various subassemblies. In particular, surgical clip applier 10 includes subassemblies for the handle portion 12, jaw assembly 18, spindle subassembly 72, and a clip advancement structure 178. For manufacturing economy, each of these subassemblies can be individually completed at separate workstations. Subsequently, the finished subassemblies may be put together in a final assembly procedure as will be described in greater detail below.

The Handle Portion Subassembly

Figure 2:
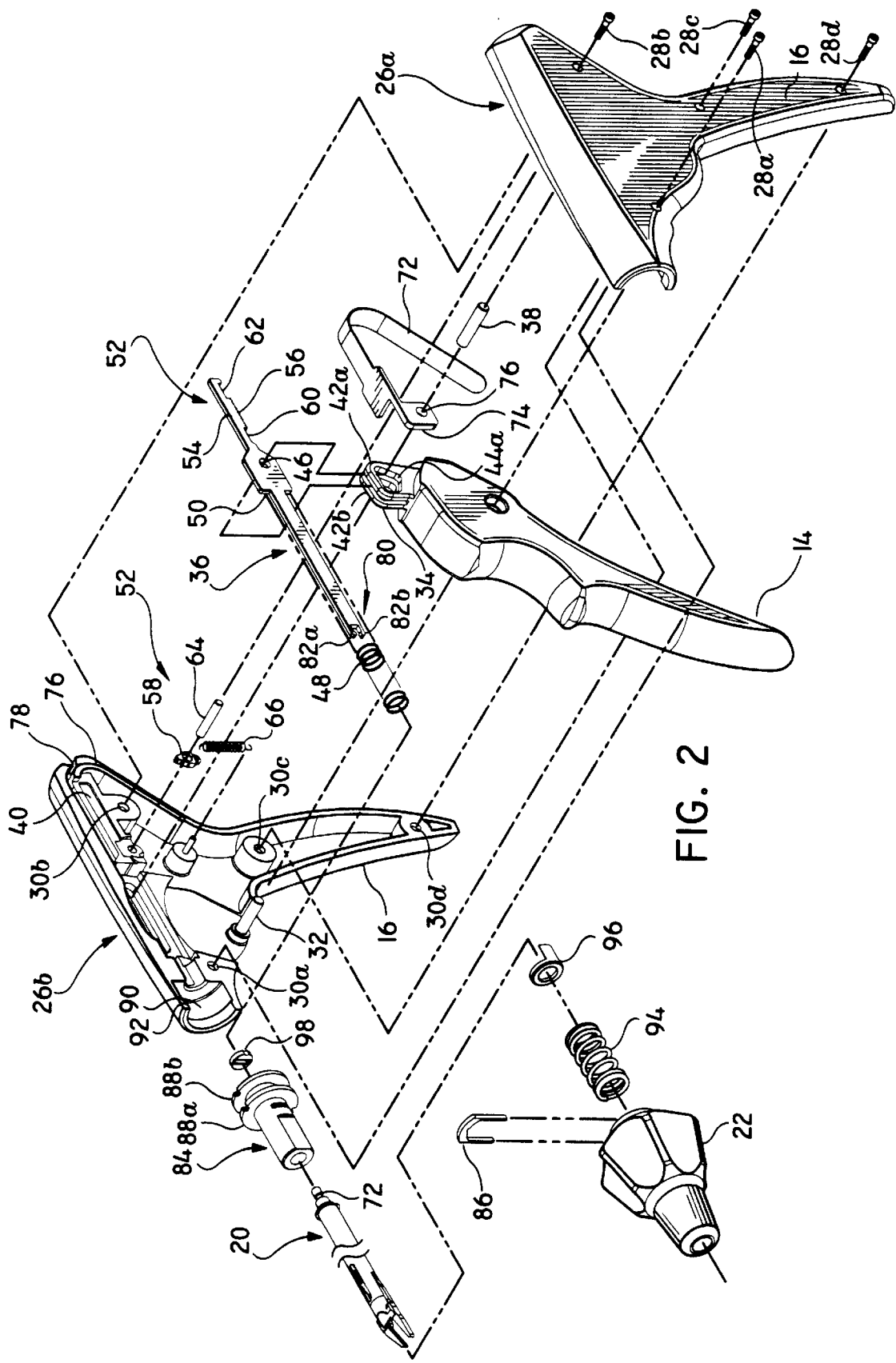
FIG. 2 is a perspective view with parts separated of the handle portion of the surgical clip applier of FIG. 1.

FIG. 2 illustrates the components of handle portion 12 of instrument 10. Handle portion 12 includes left and right housing portions 26a and 26b respectively, in which the components of the handle portion are positioned. Housing portions 26a and 26b are positioned by screws 28a, 28b, 28c and 28d inserted within apertures 30a, 30b, 30c and 30d. Housing portions 26a and 26b are alternatively secured together by sonic welding or other known means. Movable handle 14 is mounted to housing portions 26a and 26b by pin 32 which permits pivotal motion of handle 14 with respect to stationary handle 16.

Movable handle 14 further includes clevis 34 connected to a driver member, such as pusher plate 36, by contacting pin connector 38. Pusher plate 36 is mounted within recess 40 defined in housing portions 26a and 26b for reciprocal longitudinal motion therein. Clevis 34 includes a pair of spaced apart shackles 42a and 42b, each of which has an elongated aperture 44a and 44b defined therethrough for reception of pin connector 38, which is slidable therein. Apertures 44a and 44b provide a "lost-motion" feature which effectively disengages clevis 34 from pin connector 38 and drive bar 36. In particular, initial movement of movable handle 14 away from stationary handle 16 causes no movement of drive bar 36.

Pusher plate 36 is operatively connected to the jaw assembly as will be described below. Pusher plate 36 may be stamped or machined from a single piece of sheet metal or rigid engineering plastic. Pusher plate 36 includes an aperture 46 for the reception of pin connector 38. Return spring 48, configured to engage shoulder portion 50 of pusher plate 36, is provided to normally bias pusher plate 36 proximally and thereby to normally bias movable handle 14 to the open position.

Ratchet assembly 52 includes rack 54 having a plurality of ratchet teeth 56 formed on a proximal portion of pusher plate 36 and pawl 58 disposed in handle portion 12. Distal portion 60 and proximal portion 62 of rack 54 are devoid of ratchet teeth 56. Pawl 58 is rotatably mounted by pawl pin 64 and normally biased into engagement with the ratchet teeth of rack 54 by spring 66. As illustrated in FIG. 3, each of the ratchet teeth 56 on rack 54 has a substantially vertical portion and a substantially sloping portion to permit incremental distal advancement of pusher plate 36 while restricting proximal movement of pusher plate 36. Pawl 58 is provided with center tooth 68 and smaller side teeth 70a and 70b to provide positive engagement with ratchet teeth 56.

With reference to FIG. 2, flag 72 is constructed of a flexible material, such as plastic, and has a mounting portion 74 at a first end adjacent clevis 34 and is movable therewith. In particular, pin connector 38 passes through aperture 77 in mounting portion 74. The second, free end of flag 72 is slidably mounted in channel 76 adjacent the proximal end portion of housing 26a and 26b. Window 78 is defined in housings 26a and 26b to permit viewing of a portion of flag 72 therethrough. As will be described below, a marked portion 73 (not shown) of flag 72 appears in window 78 when the supply of surgical clips in surgical clip applier 10 has been depleted.

Pusher plate 36 includes bifurcated distal portion 80 having prongs 82a and 82b which facilitate rotatable mounting to an actuator, such as spindle 72. Alternatively, pusher plate 36 and spindle 72 may be connected by any other known mounting structure including, e.g. a ball-and-socket arrangement.

Rotation collar 22 provides angular rotation to spindle 72 and body 20. Rotation collar 22 is connected to bushing 84 by clip 86 and is angularly rotatable therewith. The proximal portion of bushing 84 is provided with a pair of circumferential flanges 88a and 88b, which are rotatably mounted in stepped bore 90 and secured therein by lip portion 92. Heavy gauge spring 94 and washer 96 surround bushing 84. Excessive closing force on clip applier 10 overcomes the resistance of spring 94 such that body portion 20 is distally advanced relative to handle assembly 12. This relative movement temporarily disables clip applier 10 to prevent damage. Washer 96 prevents rotation of return spring 48 during angular rotation of rotation knob 22.

Jaw Assembly Subassembly

With reference to FIG. 4, jaw assembly 18 includes elongated shank portions 100a and 100b connected at crown portion 102. Midline 104 is defined through each of shank portions 100a and 100b. The portion of jaw assembly 18 proximal to midline 104 constitutes the proximal portion of jaw assembly 18. The portion of jaw assembly 18 distal to midline 104 constitutes the distal portion of jaw assembly 18. Resilience in shank portions 100a and 100b permits relative approximation and spacing of juxtaposed jaw portions 24a and 24b. A pair of elongated channels 106a and 106b is provided on the inner surfaces of jaw portions 24a and 24b for reception of a surgical clip as will be described below. Jaw assembly 18 further includes proximal legs 108a and 108b, having a plurality of radially outwardly extending tabs 100a, 110b, 110c, and 110d formed thereon. These tabs are used for mounting and assembly as will be described in greater detail below. Longitudinal channels 112a and 112b are defined between legs 108a, 108b and crown 102 to receive corresponding guide ridges at a distal portion of spindle subassembly 72, as will be described below.

FIG. 4A illustrates, in enlarged form, a pair of position tabs 114a and 114b disposed on elongated shank portions 100a and 100b respectively, to cam jaw portions 24a and 24b as will be described below.

Figure 5:
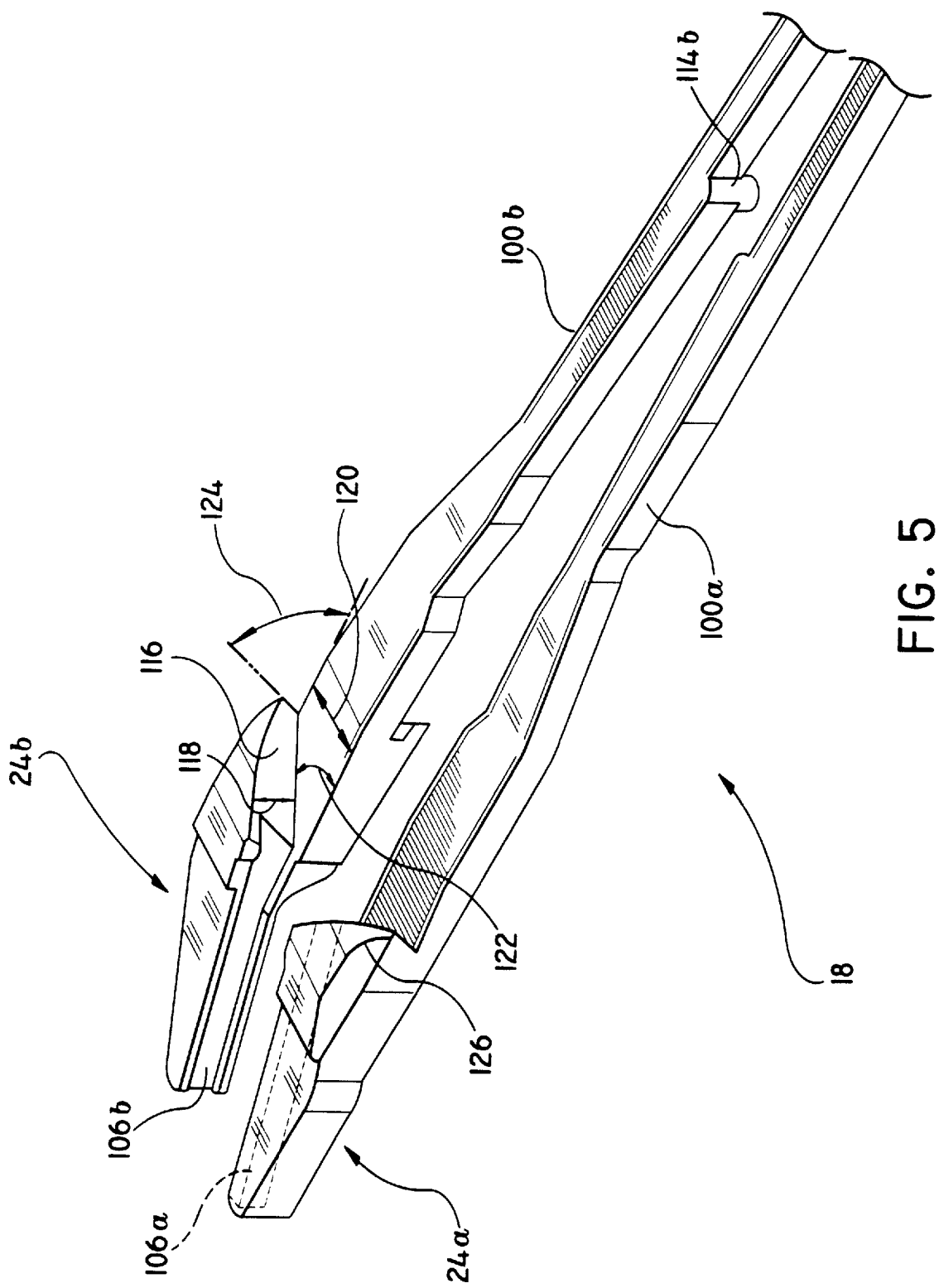
FIG. 5 is an enlarged perspective view of the jaw assembly, illustrating the target area for reception of a fastener.

As illustrated in FIG. 5, jaws 24a and 24b are configured to receive surgical fasteners into channels 106a (illustrated in phantom lines) and 106b. Reception surface or target area 116 is defined at a proximal face of each of jaws 24a and 24b at the junction with shanks 100a and 100b. In particular, target area 116 is determined by vertical height 118 and lateral width 120. Each of these dimensions is maximized to the extent possible in order to provide a large area to receive the surgical fasteners and transfer them to channels 106a and 106b. Angle 122 is defined by target area 116 with the longitudinal axis to direct fasteners laterally inward. Back-cut angle 124 is defined vertically by the plane of target area 116 and the longitudinal axis. Back-cut angle 124 of less than 90 degrees is provided and radiused portion 126 is minimized in size in order to direct fasteners downward and to prevent such fasteners from inadvertently riding over the top of jaws 24a and 24b.

Figure 6:
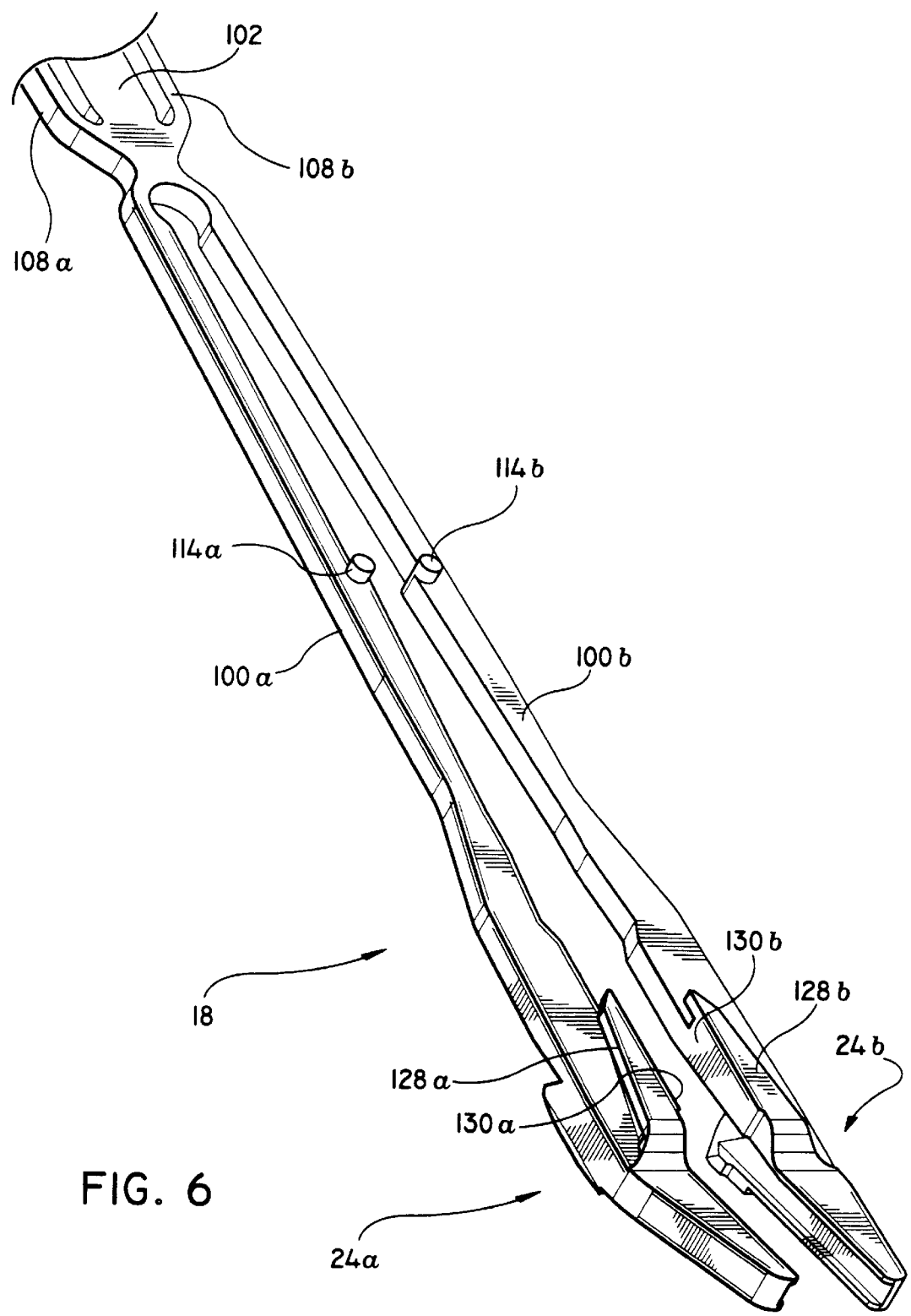
FIG. 6 is an enlarged perspective view from below of the subject clip applier, illustrating camming surfaces on the jaw portions.

Turning now to FIG. 6, each of jaw portions 24a and 24b includes raised camming surfaces 128a and 128b formed on the bottom surface thereof. Camming surfaces 128a and 128b increase in width from the proximal end to the distal end of jaws 24a and 24b. In order to provide increased closing force, camming surfaces 128a and 128b are disposed at a distal portion of jaw portions 24a and 24b adjacent inner surfaces 130a and 130b of jaw portions 24a and 24b.

Spindle Subassembly

Referring to FIG. 7, spindle subassembly 72 extends along a substantial length of body portion 20. Spindle subassembly 72 includes spindle 132, which is advanceable by handle assembly 12, and driver 134 which has a semi-circular cross-section and includes dual camming structure for opening and closing jaw portions 24a and 24b. Driver 134 is always positioned adjacent jaws 24a and 24b to provide stability for the jaws against twisting.

Linkage bar 136 and detent spring 138 are provided to interlock spindle 132 and driver 134 during a portion of the longitudinal travel of spindle 132. A distal end portion of linkage bar 136 is received in a T-slot in driver 134, and linkage bar 136 is longitudinally movable with driver 134. Detent spring 138 is pivotable within slot 139 in linkage bar 136. Linkage bar 136 includes boss 140 formed on a lower surface thereof, which is slidable in elongated slot 142 at a distal end portion of spindle 132. As illustrated in FIG. 8, detent spring 138 is normally biased upwardly and out of slot 142. This arrangement permits spindle 132 to slide while driver 134 remains stationary adjacent jaws 24a and 24b.

At a distal position in the longitudinal travel of spindle 132, detent spring 138 is moved downward into elongated slot 142 to provide a positive interlock between spindle 132 and driver 134. At such time, driver 134 is driven by spindle 132 in order to cam jaws 24a and 24b closed. Guide ridges 143a and 143b adjacent slot 142 on spindle 72 stabilize jaw assembly 18 with respect to outer sleeve 256 (not shown), as will be described below. Subsequent to closing jaws 24a and 24b, driver 134 is disengaged from spindle 132, such that driver 134 remains adjacent jaws 24a and 24b, while spindle 132 returns proximally.

Channel structure 144 on driver 134 is configured, with a groove pattern to control and cam jaw portions 24a and 24b to a spaced-apart position. Jaw closure structure 146 includes a bifurcated cam configuration to approximate jaw portions 24a and 24b about a surgical clip.

With continued reference to FIG. 7 in conjunction with FIG. 7A, a medial portion of spindle 132 includes trip lever assembly 156. Trip lever assembly 156 includes trip lever 158 mounted on spindle 132 and disposed within longitudinally aligned recess 160. Trip lever 158 is pivotably retained therein by pivot pin 162. Distal tab 164 of trip lever 156 is normally biased upward by trip lever spring 166. Trip lever 158 defines mounting aperture 168 to snap fit over pivot pin 162. Distal tab 164 includes a pair of laterally projecting pins 170a and 170b configured to engage a camming surface on clip advancement subassembly 178, as will be described below. It is contemplated that the trip lever and spring arrangement could be substituted with other equivalent structure including, e.g., a leaf spring or other resilient member.

Longitudinal recess 160 receives wedge member 172, which is longitudinally slidable therein. Wedge member 172 is connected to thrust bar 184, described below, and has an angle lower surface 174 corresponding to an angled upper surface 161 (not shown) of recess 160. Theses surfaces are configured to interact when the supply of fasteners in surgical instrument 10 has been depleted.

A hemispherical portion 176 of spindle 132 having a flat upper surface is provided distal to the trip lever assembly 156. Both hemispherical portion 176 and trip lever assembly 156 are configured to engage with clip advancement subassembly 178 as will be described below. Sealing member, such as O-ring seal 175, is positioned about an annular groove in spindle 132 to prevent escape of fluids or insufflation gases during the surgical procedure.

As illustrated in FIG. 9, channel structure 144 includes raised center block 148. A pair of longitudinally elongated parallel channels 150a and 150b extend along the sides of center block 148. Proximal zone or recess 152 is disposed proximal to center block 148. Channel structure 148 is configured to slidably receive position tabs 114a and 114b of jaw assembly 18 (See, FIG. 6).

Jaw closure structure 146 includes a bifurcated configuration having a pair of camming surfaces 154a and 154b in a tapering V-shaped configuration to cooperate with raised camming surfaces 128a and 128b on jaw assembly 18. As shown in FIGS. 10 and 11, camming surfaces 154a and 154b of driver 134 are disposed in surrounding "T-slot" arrangement with respect to raised camming surfaces 128a and 128b of jaws 24a and 24b to provide stability to the jaws during overall operation of the instrument. Distal advancement of driver 134 during interlocking engagement with spindle 132 moves jaw portions 24a and 24b into approximation.

Clip Advancement Subassembly

Turning now to FIG. 12, clip advancement subassembly 178 is depicted including upper housing 180, lower housing 182, and thrust bar or clip pusher 184. Upper housing 180 and lower housing 182, in combination, define a feed chute 186 sized and configured to facilitate the stacking of surgical clips. As illustrated in FIG. 13, upper housing 180 has a substantially semicircular or trapezoidal cross-section and includes recess 188. Upper housing 180 is connected to lower housing 182. Substantially rectangular feed chute 186 is defined by upper housing 180 and by side walls 181a and 181b and base portion 183 of lower housing 182.

With continued reference to FIG. 12, feed chute 186 stores a stack 190 of U-shaped surgical clips 192 therein, including a distalmost surgical clip 192a. Surgical clip stack 190 is configured such that legs 194c of surgical clip 192c are substantially in contact with the crown portion 196b of the next distal surgical clip 192b. The stack 190 of surgical clips 192 is urged towards the distal portion of feed chute 186 by clip follower 198 which is biased distally by follower spring 200 positioned in recess 188 of upper housing 180. The proximal end of spring 200 is retained by retainer block 202. A pair of clip stops 208a and 208b inhibit a distalmost surgical clip 192a from moving into the jaw assembly 18 by contacting the crown portion 196a of surgical clip 192a. Boss 204 on retainer block 202 is received in mounting aperture 206 at a proximal portion of lower housing 182 (FIG. 14).

As illustrated in FIG. 12, thrust bar 184 is slidable along upper surface 210 of upper housing 180. During a portion of the closing stroke of movable handle 14, thrust bar 184 is distally advanced by spindle 132 (not shown), as will be described below. Thrust bar 184 is biased proximally by return spring 212. A distal end of return spring 212 abuts retainer block 202. With reference to FIG. 14, the proximal end of return spring 212 surrounds supporting pin 214 which is retained by flange 216 on thrust bar 184. The proximal end portion of retaining block, 202 has a trip lever engaging configuration 218 formed thereon. A pair of outer sloping surfaces 220a and 220b are formed on either side of recessed, center sloping surface 222. Outer sloping surfaces 220a and 220b are configured to interact with pins 170a and 170b of trip lever 158 as will be described below.

As shown in FIG. 15, the distal end portion of thrust bar 184 includes an angularly depending portion 224 which includes a rib 225 to strengthen thrust bar 184 during advancement of surgical clips 192. A bifurcated clip engaging portion 226 has a leading edge 228 and a sloping trailing edge 230.

With reference to FIG. 16, upper housing 180 defines a plurality of recesses 232 including raised tabs 234 which receive flanges 236a, 236b including ears 237 of lower housing 182 to mount lower housing 182 and upper housing 180. Recess 188 communicates with feed chute 186, and provides access for follower spring 200 and clip follower 198 inserted therein. Lock lever 231 is formed in base portion 183 as an integrally formed cantilevered member connected to base 183 at its proximal end and extending upwardly at its distal end.

Turning now to FIG. 17, the various components of clip advancement subassembly 172 are illustrated in assembled combination. In particular, upper housing 180 and lower housing 182 are assembled. Thrust bar 184 is slidably mounted on upper housing 180.

FIG. 18 illustrates in enlarged form the position of distalmost surgical clip 192a at the distal end of feed chute 186. Legs 194a of surgical clip 192a are stabilized by side walls 181a and 181b, and crown 196a is supported by clip stops 208a and 208b. Angularly depending portion 224 of thrust bar 184 extends into feed chute 186. Leading edge 228 of clip engaging portion 226 is configured to contact crown 196a of surgical clip 192a to advance the clip beyond clip stops 208a and 208b as will be described below.

Figure 19:
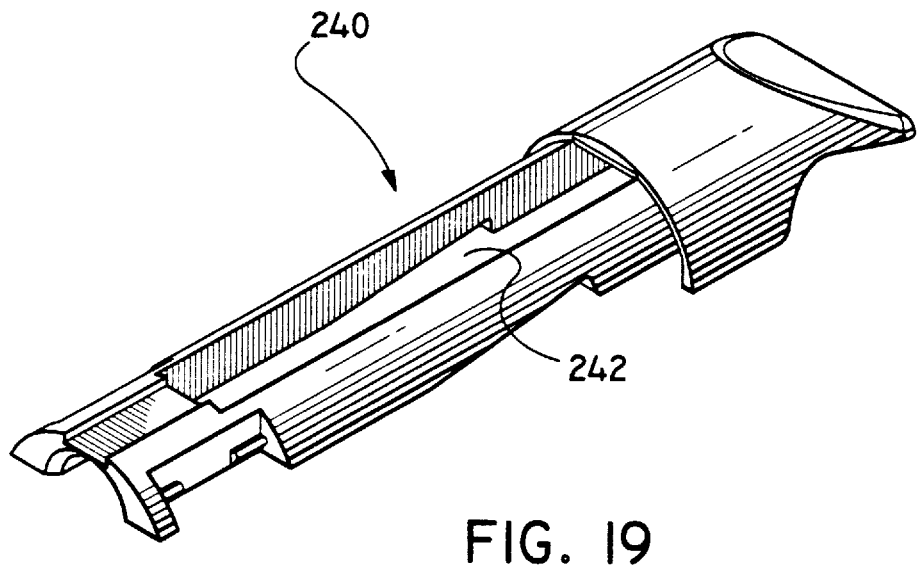
FIG. 19 is an enlarged perspective view of a referred nosepiece of the subject surgical clip applier.
Figure 20:
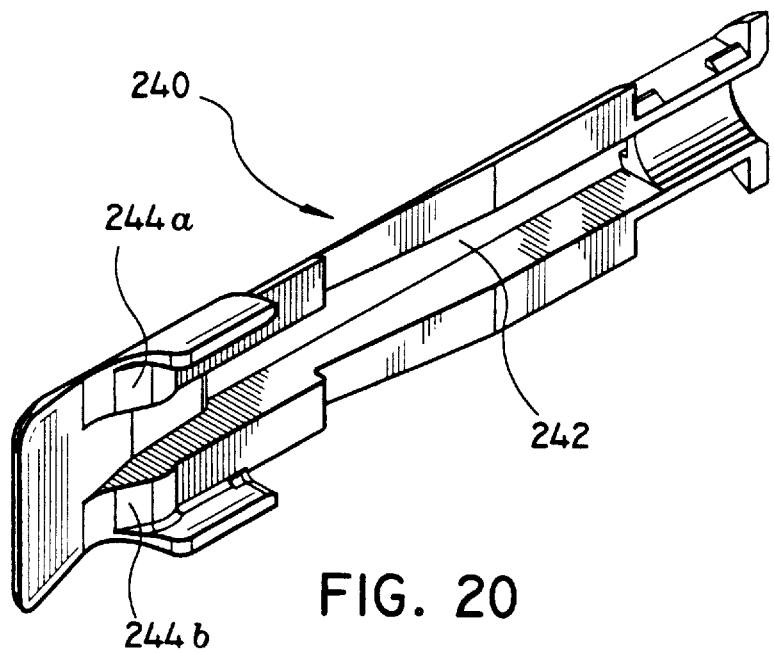
FIG. 20 is an enlarged perspective view from below of the nosepiece.

With reference to FIGS. 18–19, nosepiece 240 defines a longitudinal slot 242 to direct angularly depending portion 224 of thrust bar 184. A pair of camming surfaces 244a and 244b are defined on the bottom portion of nosepiece 240 to apply a downward force on jaw portions 24a and 24b to provide positive engagement of the jaw portions with camming structures 144 and 146 on driver 134.

Method of Assembly

Figure 21:
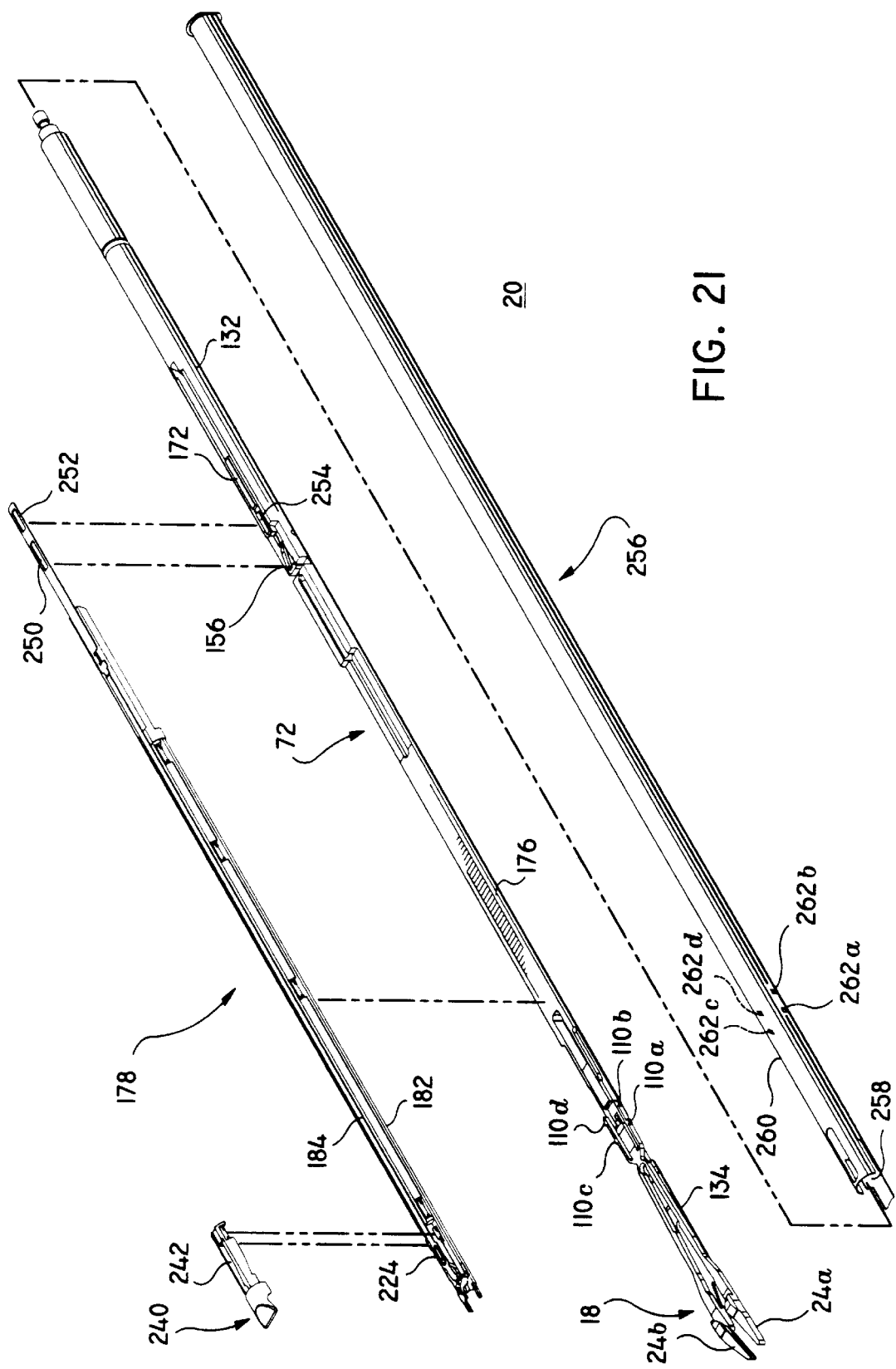
FIG. 21 is a perspective view of the subject surgical clip applier with subassemblies separated, illustrating the nosepiece, the clip advancement subassembly, the spindle subassembly, the jaw assembly, and the outer sleeve.

Having thus described the internal components and/or subassemblies of clip applier 10, the method of assembly will now be described. With reference to FIG. 21, endoscopic portion 20 is assembled from the previously described components.

Jaw assembly 18 is positioned adjacent driver 134 of spindle subassembly 72 such that jaw closing structure 146 is in surrounding engagement with raised camming surfaces 128a and 128b of jaws 24a and 24b. In addition, position tabs 114a and 114b on jaws 24a and 24b are disposed within channel structure 144 on driver 134.

As shown in FIG. 21 in conjunction with FIG. 22, nosepiece 240 is positioned adjacent lower housing 182 such that angularly depending portion 224 of thrust bar 184 is slidable within slot 242.

With reference to FIGS. 21 and 23, assembly of clip advancement subassembly 178 and spindle subassembly 72 will now be described. Lower housing 182 is configured to rest partially on hemispherical portion 176 of spindle 72 and partially on jaw assembly 18. Longitudinal slot 250 and aperture 252 are defined at a proximal portion of thrust bar 184. Longitudinal slot 250 is positioned in interlocking arrangement with trip lever assembly 156. Boss 254 on an upper surface of wedge member 172 is received in aperture 252 in thrust bar 184 such that wedge member 172 and thrust bar 184 are longitudinally movable as a unit.

With continued reference to FIG. 21, a substantially cylindrical profile is defined by the combination of spindle subassembly 72 and clip advancement subassembly 178.

Outer sleeve 256 is provided defining a cylindrical internal passage 258 therethrough having a circular cross-section. Internal passage 258 is sized to receive the assembled components described above, which are inserted into the distal end portion 260 of outer sleeve 256. Apertures 262a, 262b, 262c, and 262d at distal portion 260 of outer sleeve 256 are configured to receive tabs 110a, 110b, 110c, and 110d of jaw assembly 18 in snap-fitting arrangement.

Turning now to FIGS. 24 and 25, the assembly of endoscopic portion 20 and handle assembly 12 will now be described. Bushing 84 is slidably received in rotating collar 22. Bushing 84 includes a substantially cylindrical portion 270 defining a flat surface 272, and a lateral groove 274 (FIG. 25). Spring 94 and washer 96 are positioned about proximal portion of sleeve 256, such that flat portion 259 of flange 257 cooperates with a corresponding flat tab 97 on washer 96. Spring 94, washer 96 and body 20 are inserted in bore 23 of rotation collar 22. Cylindrical portion 270 of bushing 84 is inserted into bore 23 of rotation collar 22. U-shaped clip 86 is passed through opening 276 in rotation collar 22, such that legs 278a and 278b of clip 86 are received in grooves 274 of bushing 84, as shown in FIG. 27.

Return spring 48 and washer 98 are positioned within bore 275 over pusher plate 36 (FIG. 26). Bifurcated distal portion 80 of pusher plate 36 is connected to a proximal mounting portion 278 of spindle 72. In particular, annular notch 280, is configured to be received by prongs 80a and 80b for angular rotation of spindle 72 with respect to pusher plate 36. Peripheral fins 88a and 88b of bushing 84 are retained in housing by circumferential flange 92.

Overall Operation of Clip Applier

Having thus described the internal components and assembly of clip applier 10, the operation thereof will now be described. With reference to FIGS. 28 and 29, clip applier 10 is initially disposed with movable handle 14 in the open or "at-rest" position. Pusher plate 36 is positioned in a proximal position with respect to housing portions 26a and 26b. As illustrated in FIGS. 30–31, driver 134 is disposed adjacent jaws 24a and 24b. Position tabs 114a and 114b of jaw assembly 18 are disposed in channel structure 144, and more particularly in parallel channels 150 a and 150b. Consequently, jaw portions 24a and 24b are maintained in a spaced-apart position. Further, camming surfaces 154a and 154b are in engagement with raised camming surfaces 128a and 128b of jaws 24a and 24b. Movable handle 14 is maintained in the "at-rest" position during insertion of body portion 20 and jaw assembly 18 through the cannula.

When the surgeon has placed the jaw assembly 18 adjacent the surgical site, a single closing stroke of movable handle 14 towards stationary handle 16 is sufficient to first deploy and/or ensure that the jaw portions 24a and 24b are in a spaced apart position adjacent or around the tissue or structure to be crimped, to sequentially advance a clip to the spaced-apart jaw portions, to reposition the clip-containing jaw portions, as desired, and to finally deform the clip on the desired structure. Closure from the "at-rest" position of movable handle 14 to an intermediate position constitutes an initial throw thereof. Finally, closure from the intermediate position to the closed position constitutes a final throw.

The beginning of the initial throw is shown in FIGS. 32–39. As illustrated in FIG. 33, clevis 34 engages pin connector 38 such that pusher plate 36 and spindle 132 advance distally against the bias of spring 48. Pawl 58 is in engagement with rack 54 to index incremental advancement of pusher plate 36 and prevent pusher plate 36 from returning proximally.

Figure 34:
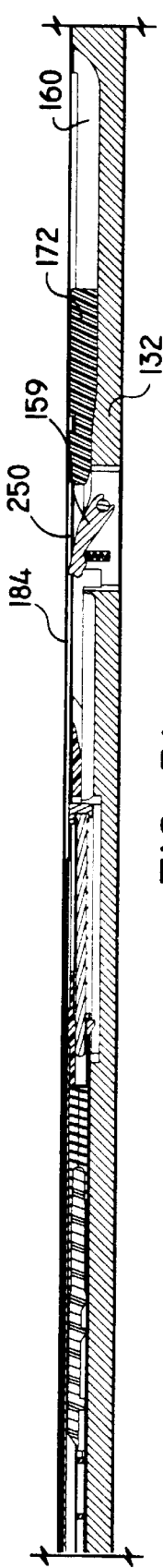
FIG. 34 is an enlarged cross-sectional view of the endoscopic portion, illustrating interlocking of a trip lever on the spindle with the thrust bar of the instrument in the progressive actuation position of FIG. 32.
Figure 35:
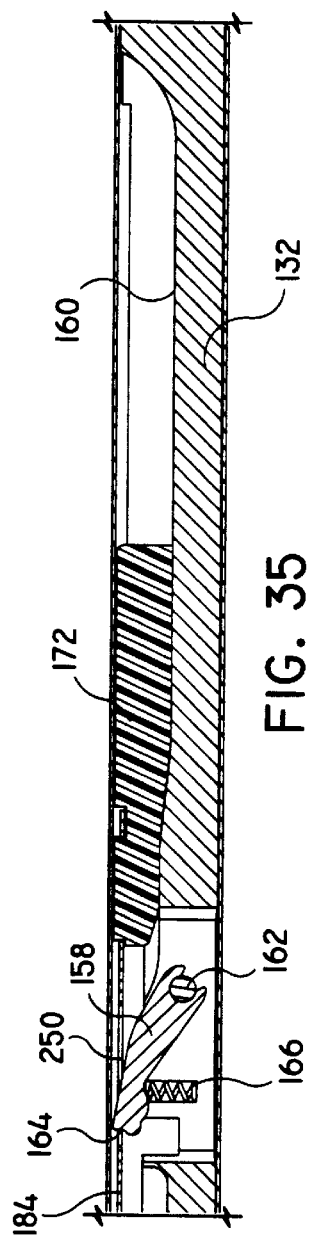
FIG. 35 is an enlarged cross-sectional view of the endoscopic portion of FIG. 34.
Figure 36:
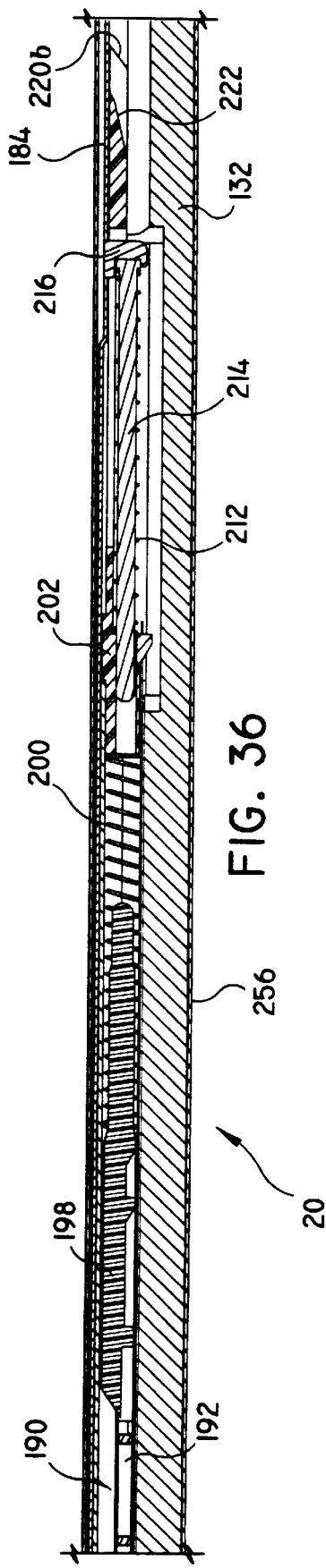
FIG. 36 is an enlarged cross-sectional view of the endoscopic portion, illustrating a feed chute, a clip follower, and a stack of surgical clips of the instrument in the progressive actuation position of FIG. 32.

With reference to FIGS. 34–35, thrust bar 184 moves distally with spindle 132 due to locking engagement of distal tab 164 of trip lever 158 with slot 250 of thrust bar 184. FIG. 36 depicts clip follower 198 in biased relationship with the stack 190 of surgical clips 192.

Figure 37:
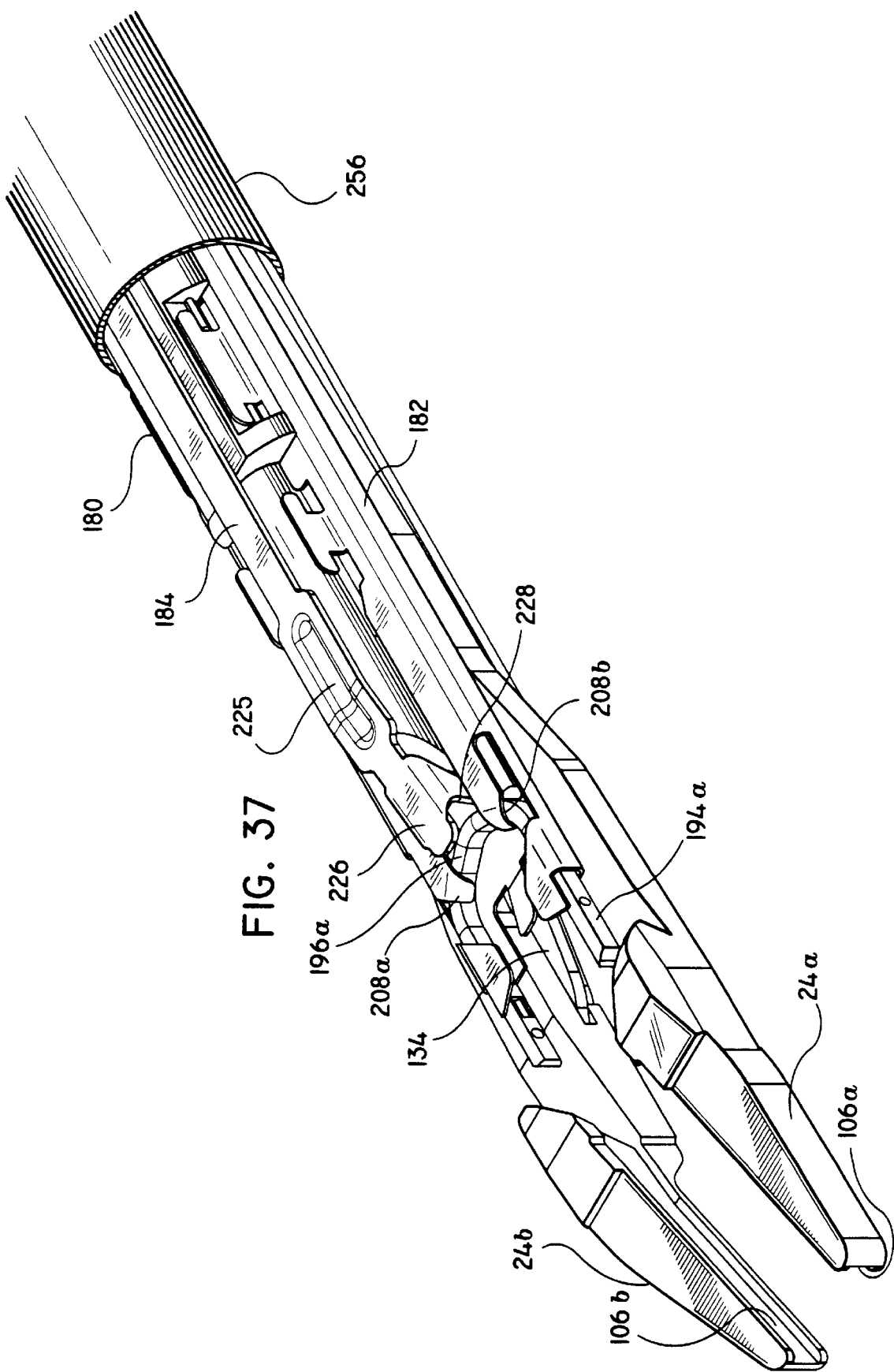
FIG. 37 is an enlarged perspective view of the jaw assembly prior to advancement of a surgical clip by the thrust bar.

In FIGS. 37–38, clip engaging portion 226 engages the crown 196a of the distalmost surgical clip 192a against the restraining force of clip stops 208a and 208b. Further advancement of thrust bar 184 advances surgical clip 192a beyond clip stops 208a and 208b as shown in FIG. 39. Clip camming surface 282 contacts crown 196a and directs legs 194a of surgical clip 192a into channels 106a and 106b on the inner surfaces of jaw portions 24a and 24b. The spacing of jaw portions 24a and 24b is selected such that a tight frictional grip is created between jaw portions 24a and 24b and surgical clip 192a to prevent surgical clip 192a from falling out of the jaw portions.

Figure 41:
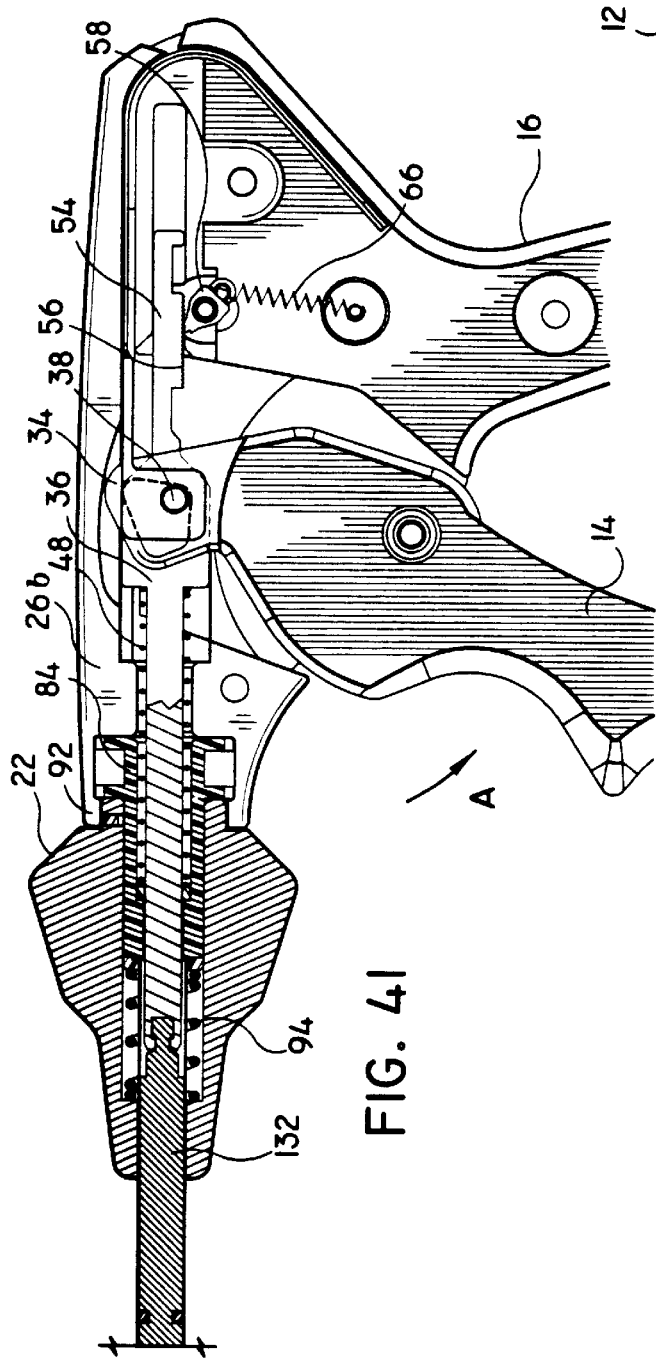
FIG. 41 is an enlarged cross-sectional view of the handle portion of the instrument in the actuation position of FIG. 40.
Figure 40:
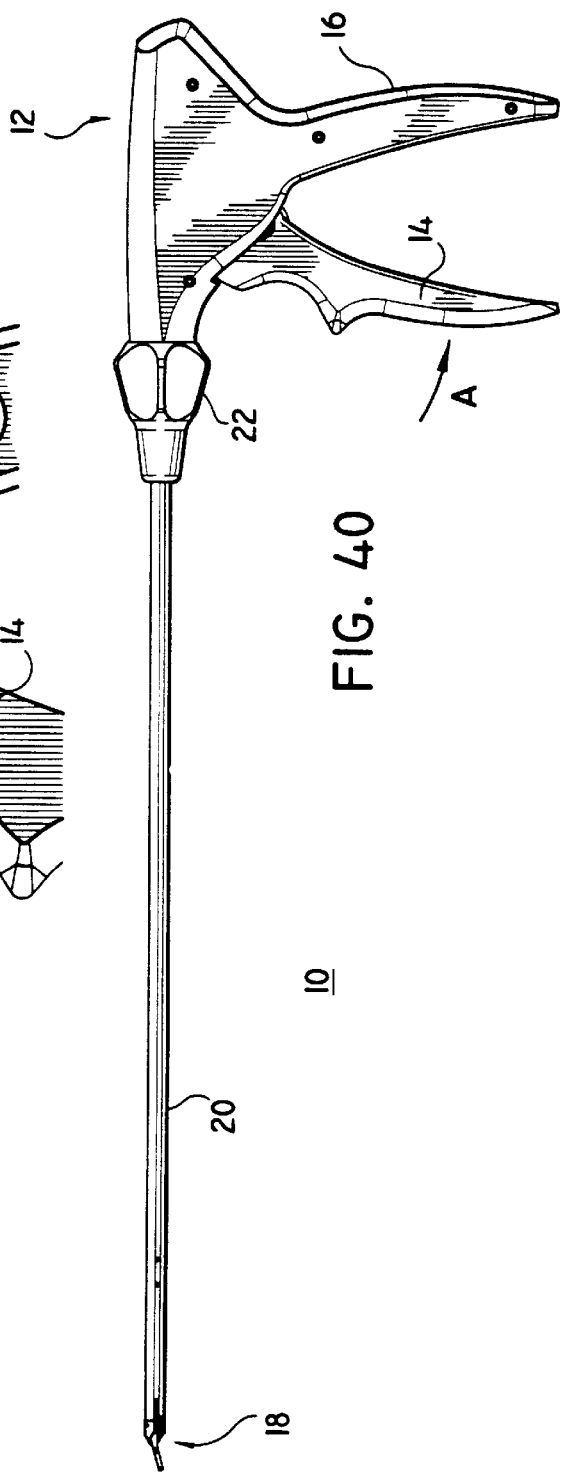
FIG. 40 is a side view of the subject surgical clip applier, illustrating the movable handle at an intermediate throw of the closing stroke.

Referring to FIGS. 40–46, the operation of the end portion of the initial stroke will now be described. As illustrated in FIG. 41, movable handle 14 continues to operably advance pusher plate 36 distally. Pawl 58 is engaged with the ratchet teeth 56 on rack 54 to index advancement of spindle 132 and to prevent proximal movement thereof during clip advancement. As illustrated in FIG. 42, clip engaging portion 226 has advanced surgical clip 192a into channels 106a (not shown) and 106b in the jaw portions.

Referring to FIG. 43, spindle 132 advances trip lever 158 such that laterally projecting pins 170a and 170b contact sloping surfaces 220a and 220b on mounting block 202. As illustrated in FIG. 44, trip lever 158 pivots about pin 162 in the direction of arrow "C" against the bias of spring 166, and distal tab 164 moves downward and out of slot 250 in thrust bar 184. Thrust bar 184 returns proximally in the direction of arrow "P" due to the bias of return spring 212. Spindle 132 continues to move distally as shown in FIG. 45. The resilience of angled portion 224 and the shallow slope of trailing edge 230 enable clip engaging portion 226 to ride over crown 196b of the next surgical clip 192b, as shown in FIG. 46.

Figures 48, 49:
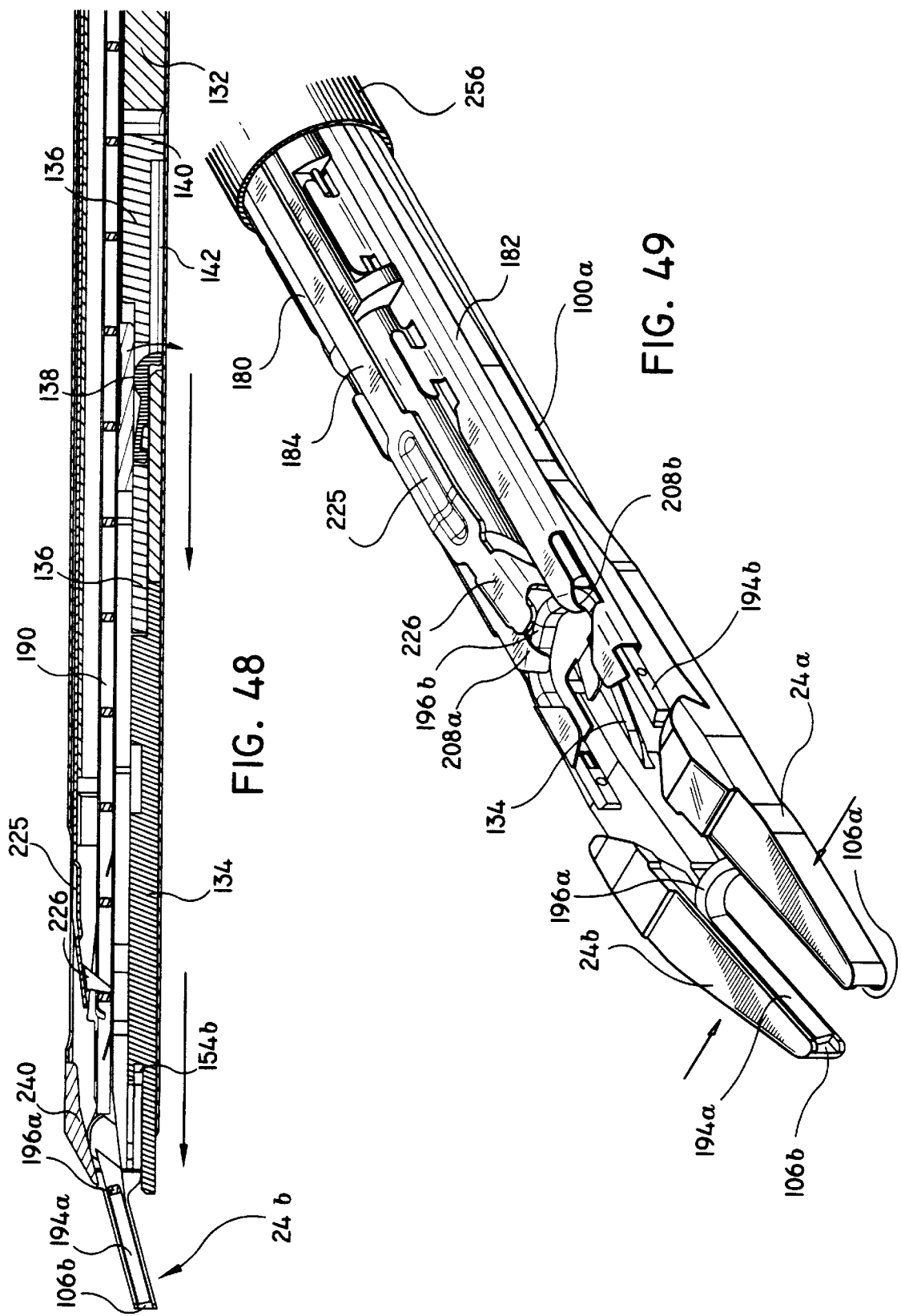
FIG. 48 is an enlarged cross-sectional view of the endoscopic portion, illustrating the detent spring disposed in engagement with the spindle, and the driver and spindle moving distally.
FIG. 49 is an enlarged perspective view of the jaw assembly, illustrating the closure of the jaw portions to deform the surgical clip disposed therebetween.

With reference to FIG. 47 in conjunction with FIG. 48, handle 14 is moved through the final throw towards the closed position. Pawl 58 is disposed in the proximal zone 62 of rack 54 that is devoid of teeth 56. As illustrated in FIG. 48, as spindle 132 moves distally, crown portion 102 of jaw assembly 18 contacts detent spring 138, which is pivoted downward into slot 142 at the distal end portion of spindle 132. Continued advancement of spindle 132 likewise advances linkage bar 136 and driver 134.

As illustrated in FIGS. 49–51, jaws 24a and 24b are cammed into approximation by driver 134. With reference to FIG. 50, position tabs 114a and 114b pass from the parallel channels 150a and 150b to the proximal zone 152, in which jaw portions 24a and 24b are freely movable. Camming surfaces 154a and 154b on jaw closure structure 146 of driver 134 begin to engage raised camming surfaces 128a and 128b on jaw portions 24a and 24b. Guide ridges 143a and 143b at distal end portion of spindle 132 are advanced into channels 112a and 112b between crown 102 and proximal legs 108a and 108b of jaw assembly 18. Guide ridges 143a and 143b exert lateral force on proximal legs 108a and 108b, thereby maintaining tabs 110a, 110b, 110c, 110d in apertures 262a, 262b, 262c, 262d and thereby preventing jaw assembly 18 from being ejected distally from sleeve 256.

Referring to FIGS. 52–53, jaw portions 24a and 24b are gradually brought into approximation with distal movement of driver 134. In particular, raised camming surfaces 128aand 128b are wider at the distal portion than at the proximal portion. Therefore, progressive movement of V-shaped jaw closure structure 146 cams jaw portions 24a and 24b closed. The proximity of jaw closure structure 146 and camming surfaces 154a and 154b to the distal portion of jaw portions 24a and 24b enables sufficient force to be exerted on jaw portions 24a and 24b to deform clip 192 (not shown) and compress blood vessels or other body tissue surrounded thereby.

As illustrated in FIGS. 54–58, the sequence of movements during the return stroke of handle 14 will be described. As shown in FIG. 54, handle 14 moves to the open position due to the normal bias of return spring 48 (not shown). Spindle 132 and driver 134 are moved proximally due to the interlocking of detent spring 138 in slot 142 of spindle 132 (FIG. 55). As driver 134 moves proximally, position tabs 114a and 114b are moved from proximal zone 152 into parallel slots 150a and 150b, as shown in FIG. 56. Further proximal movement of driver 134 is restrained by engagement of position tabs 114a and 114b with the distal portions of parallel slots 150a and 150b. Simultaneously, detent spring 138 is positioned proximal to crown portion 102 as shown in FIG. 57. The normal upward bias of detent spring 138 moves spring 138 out of engagement with slot 142. As illustrated in FIG. 58, spindle 132 is permitted to move proximally, while driver 134 remains stationary adjacent jaws 24a and 24b.

Turning now to FIGS. 59–65, a disabling feature of clip applier 10 will now be described. As shown in FIG. 59, application of excessive force to clip applier 10 in closing handle 14 may occur, e.g., if jaws 24a and 24b (not shown) are applied to resistant tissue. As described above, driver 134 applies force to jaw assembly 18 to cam jaws 24a and 24b closed. The application of excessive force to driver 134 may eject jaw assembly 18 from sleeve 256 or otherwise damage jaw assembly 18. Sleeve 256 is normally biased in a proximal position by spring 94. More particularly, a proximal end of spring 94 biases washer 96 against flange 257 of sleeve 256. Spring 94 is rated to compress under a high degree of force. During normal operation of clip applier 10, the force exerted on spring 94 is insufficient to compress spring 94. Consequently, sleeve 256 is maintained in a stationary position as spindle 132 is advanced distally. When the force applied to instrument 10 exceeds the rating of spring 94, spring 94 begins to compress, as shown in FIG. 60. As spring 94 compresses, washer 96 moves distally, thereby moving sleeve 256 distally therewith to disable the clip applier.

Clip follower 198 is advanced distally as each surgical clip 192 is applied. After the stack 190 of surgical clip 192 has been depleted, clip follower 198 is positioned at the distal end portion of lower housing 182, as illustrated in FIG. 61. Clip follower 198 includes body portion 286 and legs 288a and 288b, as shown in FIG. 62. Angled nosepiece 290 is formed at the distal end of body 286. Legs 288a and 288b are joined to body portion 286 at shoulder portions 292a and 292b, which are engaged by clip stops 208a and 208b. Web 294a is positioned between body 286 and leg 288a. Similarly, web 294b is positioned between body 286 and leg 288b. FIG. 63 illustrates recess 296 defined on a bottom surface of clip follower 198. Recess 296 has a substantially vertical abutment face 298 (FIG. 64).

Clip follower 198 is distally advanced in feed chute 186 until clip stops 208a and 208b engage shoulder portions 292a and 292b. Lock lever 231 is deflected downward in a flattened position until recess 296 of clip follower 198 is positioned over lock lever 231. As illustrated in FIG. 64, lock lever 231 is permitted to move upward into recess 296, and engagement of lock lever 231 against abutment face 298 restrains clip follower 198 from moving proximally. Thrust bar 184 begins an initial proximal movement after trip lever 158 is pivoted out of engagement with thrust bar 184 (See, FIGS. 43–45). Thrust bar 184 is prevented from moving proximally due to the positioning of clip follower 198 at the distal end of feed chute 186. In particular, bifurcated distal portion 226 of thrust bar 184 contacts webs 294a (not shown) and 294b and angled nosepiece 290 of clip follower 198, thereby forcing thrust bar 184 upward against camming surfaces 244a and 244b of nosepiece 240 and forcing rib 225 against body 286 of clip follower 198. Clip follower 198 acts as a blocking mechanism to prevent movement of the thrust bar 184. In particular, thrust bar 184 is restrained from further proximal movement due to the insufficient clearance between nosepiece 240 and clip follower 198.

Figure 65:
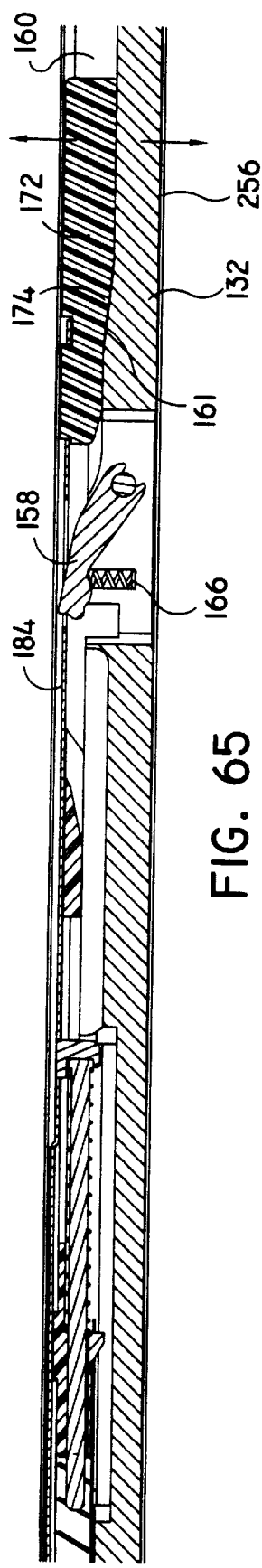
FIG. 65 is a cross-sectional view of the endoscopic portion illustrating the clip pusher in restrictive engagement with the spindle.

As FIG. 65 illustrates, when thrust bar 184 is blocked in a distal position, wedge member 172 is likewise prevented from moving proximally within slot. During the return travel of spindle 132, angled surface 161 of slot 160 is brought into approximation with angled surface 174 of stationary wedge member 172. Interaction of angled surfaces 174 and 161 causes wedge member 172 and spindle 132 to be moved radially outward against the inner surface of sleeve 256 as indicated by the arrows. Such movement of wedge member 172 and spindle 132 binds these components from further movement and effectively disables instrument 10.

Figure 66:
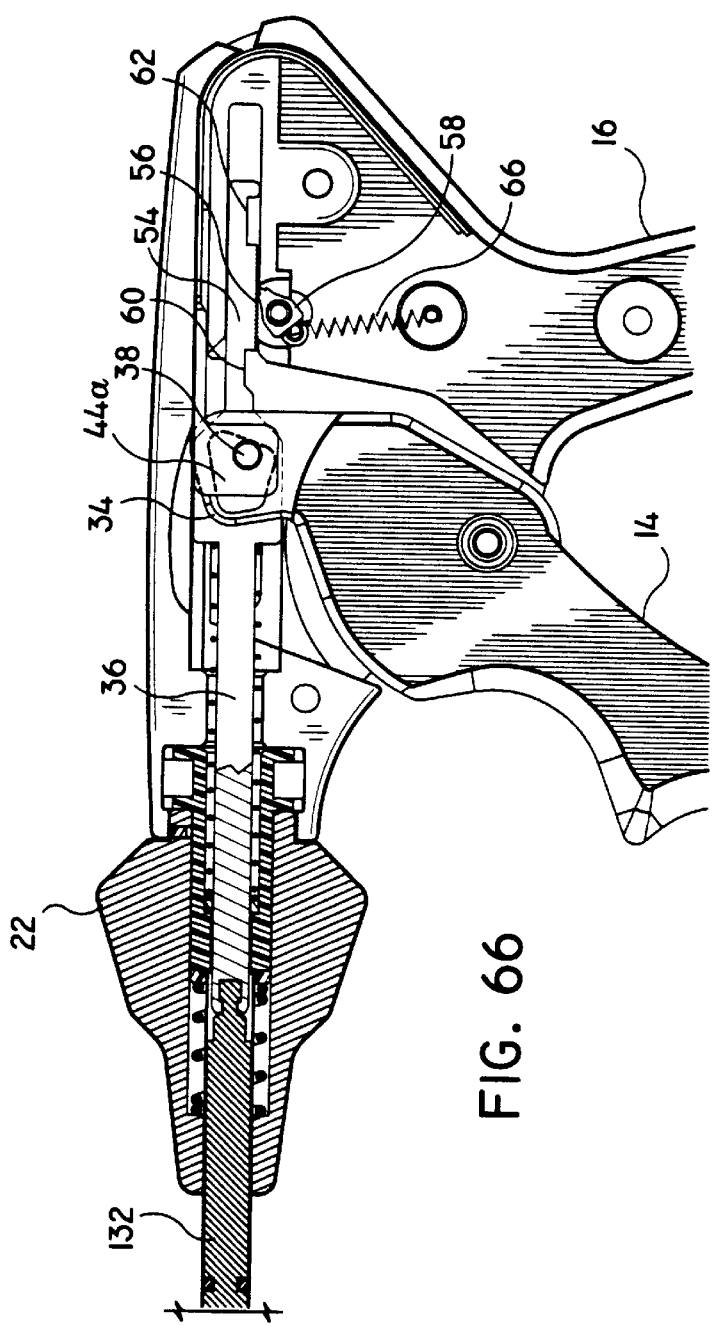
FIG. 66 is an enlarged cross-sectional view of the handle assembly, illustrating the pawl in engagement with the ratchet after closure of the movable handle.
Figure 67:
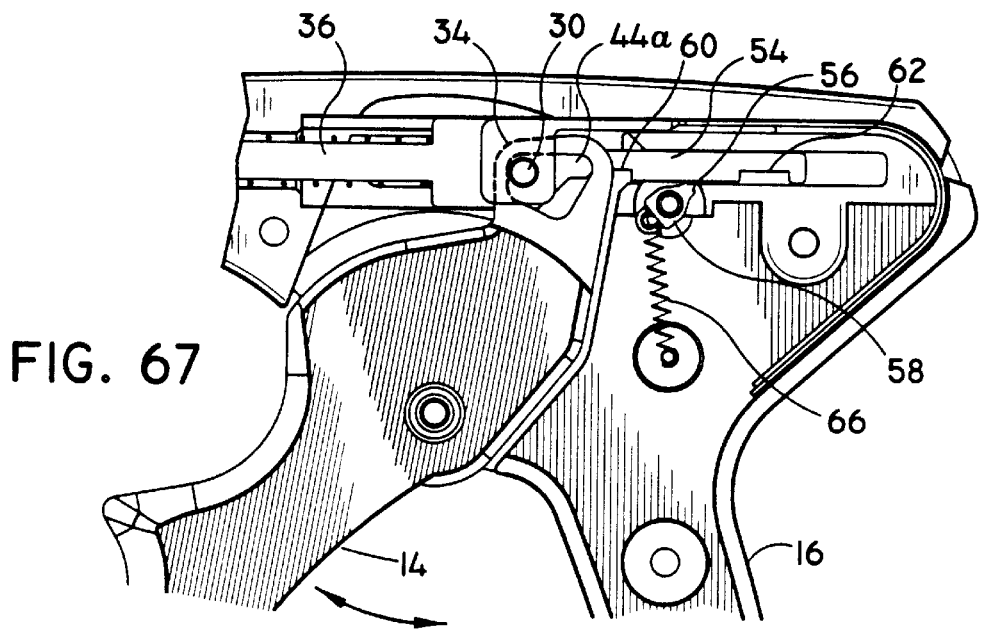
FIG. 67 is an enlarged cross-sectional view of the handle assembly, illustrating the lost motion configuration of the movable handle.
Figure 68:
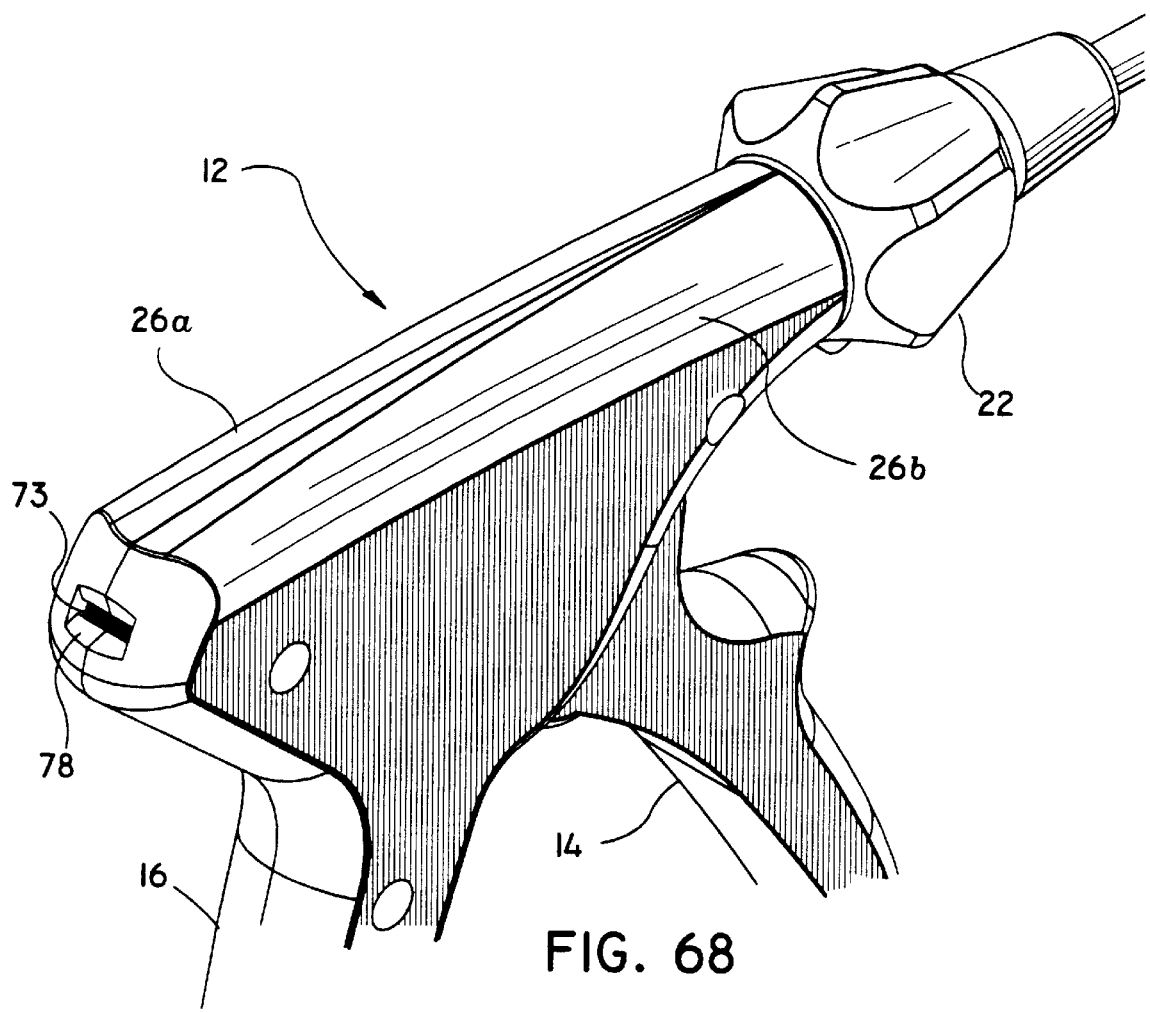
FIG. 68 is a perspective view of the proximal portion of the handle assembly, illustrating the indicator window.

With reference to FIG. 66–67, apertures 44a and 44b, in clevis 34 are configured such that no motion is transferred from handle 14 to pin 38 during partial opening of handle 14. This configuration prevents handle 14 from being opened to forcibly overcome interaction of wedge member 172 and spindle 132. Upon disablement of instrument 10, marked portion 73 on flag 72 is displayed in window 78 to provide a visual indication that the clip supply has been depleted (FIG. 68).

It will be understood that various modifications may be made to the embodiments shown herein. For example, the jaw assembly and endoscopic portions may be sized to be accommodated in cannula assemblies of various sizes. Therefore, the above description should not be construed as limiting, but merely as exemplifications as preferred embodiments. Those skilled in the art will envision other modifications within the scope and spirit of the claims appended hereto.

What is claimed is:

1. An apparatus for application of surgical clips to body tissue, which comprises:
 a) a handle portion;
 b) a body extending distally from the handle portion and defining a longitudinal axis;
 c) a plurality of surgical clips disposed within the body;
 d) a jaw assembly mounted adjacent a distal end portion of the body, the jaw assembly including first and second jaw portions movable between a spaced-apart and an approximated position;
 e) a clip pusher configured to individually distally advance a surgical clip to the jaw assembly while the jaw portions are in the spaced-apart position;
 f) an actuator at least partially disposed within the body and longitudinally movable in response to actuation of the handle portion; and
 g) a jaw closure member positioned adjacent the first and second jaw portions to move the jaw portions to the approximated position, the actuator and the jaw closure member including interlocking structure, the interlocking structure being movable from an unlocked position to an interlocked position during a portion of the longitudinal movement of the actuator to produce corresponding movement of the actuator and the jaw closure member wherein in the unlocked position, the actuator and the jaw closure member are longitudinally movable relative to each other.

2. An apparatus as recited in claim 1, wherein the jaw closure member includes a abutment portion engaged with the first and second jaw portions to stabilize the jaw portions.

3. An apparatus as recited in claim 2, wherein the jaw closure member includes camming structure which cooperates with camming surfaces on the first and second jaw portions.

4. An apparatus as recited in claim 3, wherein the first and second jaw portions each defines a reception surface for receiving a surgical clip, the reception surface defining an angle with the longitudinal axis of less than 90 degrees.

5. An apparatus as recited in claim 1, which further comprises a release to disengage the interlock between the clip pusher and the actuator.

6. An apparatus for application of surgical clips to body tissue, which comprises:
   a) a handle portion;
   b) a body extending distally from the handle portion and defining a longitudinal axis;
   c) a plurality of surgical clips disposed within the body;
   d) a jaw assembly mounted adjacent a distal end portion of the body, the jaw assembly including first and second jaw portions movable between a spaced-apart and an approximated position;
   e) a clip pusher movably mounted to individually distally advance a surgical clip to the jaw assembly while the jaw portions are in the spaced-apart position;
   f) an actuator at least partially disposed within the body and longitudinally movable in response to actuation of the handle portion;
   g) a jaw closure member positioned adjacent the first and second jaw portions, the actuator and the jaw closure member including interlocking structure, the interlocking structure being movable from an unlocked position to an interlocked position to produce corresponding movement of the actuator and the jaw closure member when the actuator is positioned adjacent the distal end portion of the body, wherein in the unlocked position, the actuator and the jaw closure member are longitudinally moveable relative to each other.

7. An apparatus as recited in claim 6, wherein the jaw closure member includes a abutment portion engaged with the first and second jaw portions to stabilize the jaw portions.

8. An apparatus as recited in claim 6, which further includes a blocking mechanism to prevent movement of the clip pusher when the plurality of surgical clips has been applied.

9. An apparatus as recited in claim 8, wherein the clip pusher and the actuator define a jamming mechanism to prevent movement of the clip pusher and the actuator when the plurality of surgical clips has been applied.

10. An apparatus as recited in claim 6, which further comprises a visual indicator on the handle portion that the plurality of surgical clips has been applied.

11. An apparatus as recited in claim 6, wherein a handle portion includes a ratchet mechanism to index progressive longitudinal movement of the actuator.

12. An apparatus as recited in claim 6, wherein the ratchet mechanism includes a rack and a pawl having a plurality of teeth.

13. An apparatus for application of surgical clips to body tissue, which comprises:
   a) a handle portion having a first handle and a second handle mounted for relative movement, the handles defining a single closing stroke between an open position and a closed position, the closing stroke defining an initial throw and a final throw;
   b) a body extending distally from the handle portion and defining a longitudinal axis;
   c) a plurality of surgical clips disposed within the body;
   d) a jaw assembly mounted adjacent a distal end portion of the body, the jaw assembly including first and second jaw portions movable between a spaced-apart and an approximated position;
   e) a clip pusher configured to individually distally advance a surgical clip to the first and second jaw portions while the jaw portions are in the spaced-apart position during the initial throw of the handles;
   f) an actuator at least partially disposed within the body and longitudinally movable in response to actuation of the handle portion;
   g) a jaw closure member positioned adjacent the first and second jaw portions, the actuator and the jaw closure member including interlocking structure, the interlocking structure being moveable from an unlocked position to an interlocked position to produce corresponding movement of the actuator and the jaw closure member during the final throw of the handles wherein in the unlocked position, the actuator and the jaw closure member are longitudinally movable relative to each other.

14. An apparatus as recited in claim 13, wherein the jaw closure member includes a abutment portion engaged with the first and second jaw portions to stabilize the jaw portions.

15. An apparatus as recited in claim 13, which further includes a blocking mechanism to prevent movement of the clip pusher when the plurality of surgical clips has been applied.

16. An apparatus as recited in claim 15, wherein the clip pusher and the actuator define a jamming mechanism to prevent movement of the clip pusher and the actuator when the plurality of surgical clips has been applied.

17. An apparatus as recited in claim 16, the jamming mechanism includes surfaces on the clip pusher and actuator configured to produce a frictional engagement between the clip pusher, the actuator and the body.

18. An apparatus as recited in claim 13, which further comprises a visual indicator on the handle portion that the plurality of surgical clips has been applied.

19. An apparatus as recited in claim 13, wherein the handles define a pivoting movement between a closed position and an open position, the handle portion including a disengagement mechanism to disengage the handle portion from the actuator during a portion of the return pivoting movement.

* * * * *